US012649069B2

(12) United States Patent (10) Patent No.: US 12,649,069 B2

Puleo et al. (45) Date of Patent: Jun. 9, 2026

(54) NEUROMODULATION TECHNIQUES

(71) Applicant: GE Precision Healthcare LLC, Wauwatosa, WI (US)

(72) Inventors: Christopher Michael Puleo, Niskayuna, NY (US); Victoria Eugenia Cotero, Troy, NY (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 18/812,581

(22) Filed: Aug. 22, 2024

(65) Prior Publication Data

US 2024/0408415 A1 Dec. 12, 2024

Related U.S. Application Data

(63) Continuation of application No. 18/308,365, filed on Apr. 27, 2023, now Pat. No. 12,090,346, which is a continuation of application No. 17/208,547, filed on Mar. 22, 2021, now Pat. No. 11,660,474, which is a continuation of application No. 16/116,674, filed on Aug. 29, 2018, now Pat. No. 10,974,079.

(51) Int. Cl.
*A61B 5/00* (2006.01)
*A61N 7/00* (2006.01)

(52) U.S. Cl.
CPC ........ *A61N 7/00* (2013.01); *A61N 2007/0026* (2013.01)

(58) Field of Classification Search
CPC .................... A61N 7/00; A61N 2007/0026
See application file for complete search history.

(56) References Cited

U.S. PATENT DOCUMENTS

| | | | |
|---|---|---|---|
| 7,418,292 B2 | 8/2008 | Schafer | |
| 8,591,419 B2 | 11/2013 | Tyler | |
| 2009/0187230 A1 | 7/2009 | Dilorenzo | |
| 2011/0190668 A1 | 8/2011 | Mishelevich | |
| 2011/0251527 A1 | 10/2011 | Kushculey | |
| 2011/0257561 A1 | 10/2011 | Gertner et al. | |
| 2013/0096471 A1* | 4/2013 | Slayton | A61B 8/14 601/3 |
| 2013/0158452 A1 | 6/2013 | Juto et al. | |
| 2013/0237780 A1 | 9/2013 | Beasley et al. | |
| 2015/0190634 A1 | 7/2015 | Rezai et al. | |
| 2016/0001096 A1 | 1/2016 | Mishelevich | |

(Continued)

FOREIGN PATENT DOCUMENTS

| | | |
|---|---|---|
| JP | 2011527931 A | 11/2011 |
| WO | 2017192754 A1 | 11/2017 |

(Continued)

OTHER PUBLICATIONS

JP application 2024-052439 filed Mar. 27, 2024—office action issued Mar. 26, 2025; Machine Translation; 6 pages.

(Continued)

*Primary Examiner* — Joel F Brutus

(74) *Attorney, Agent, or Firm* — Fletcher Yoder, P.C.

(57) ABSTRACT

The subject matter of the present disclosure generally relates to techniques for applying mechanical or ultrasound energy to a region of interest in a subject to induce modulation of one or more nerve pathways. The region of interest may include at least a portion of a nerve ganglion.

16 Claims, 8 Drawing Sheets

(56) References Cited

U.S. PATENT DOCUMENTS

| | | | | |
|---|---|---|---|---|
| 2016/0128767 | A1 | 5/2016 | Azamian et al. | |
| 2017/0007853 | A1 | 1/2017 | Alford | |
| 2017/0100605 | A1 | 4/2017 | Schwab et al. | |
| 2018/0028841 | A1 | 2/2018 | Konofagou et al. | |
| 2018/0117017 | A1* | 5/2018 | Nemechek | A61K 36/63 |
| 2018/0117319 | A1* | 5/2018 | Chew | A61N 1/3605 |
| 2018/0133460 | A1* | 5/2018 | Townley | A61B 5/0538 |
| 2018/0147260 | A1 | 5/2018 | Bright | |

FOREIGN PATENT DOCUMENTS

| | | | |
|---|---|---|---|
| WO | 2018081763 | A1 | 5/2018 |
| WO | 2018081826 | A1 | 5/2018 |

OTHER PUBLICATIONS

Torres-Rosas, Rafael, et al.; "Dopamine Mediates the Vagal Modulation of the Immune System by Electroacupunture", HHS Public Access Author Manuscripts; vol. 20, Issue3, pp. 291-295, Mar. 2014.

Kim, Kyoung Min, M.D., et al.; "Therapeutic Approach of Wrist Ganglion Using Electroacupuncture: Two Case Reports"; Annals of Rehabilitation Medicine (ARM), vol. 38, Issue 3, pp. 415-420; Jun. 26, 2014.

Meyers, Erin E., et al.; "Contrasting Effects of Afferent and Efferent Vagal Nerve Stimulation on Insulin Secretion and Blood Glucose Regulation"; Physiological Reports 4 (4), pp. 1-9, 2016.

Jiang, Qiuju, et al.; "Temporal Neuromodulation of Reinal Ganglion Cells by Low-Frequency Focused Ultrasound Stimulation"; EMB IEEE Transactions on Neural Systems and Rehabilitation Engineering, vol. 26, No. 5, pp. 969-970; May 2018.

Tyler, William J., et al.; "Ultrasonic Modulation of Neural Circuit Activity"; Current Opinion in Neurobiology, vol. 50, pp. 222-231; Jun. 2018.

PCT/US2019/048624; International Search Report/Written Opinion mailed Nov. 14, 2019; pp. 1-15.

PCT/US2019/048624; International Preliminary Report on Patentability mailed Mar. 11, 2021; pp. 1-9.

JP application 2024-052439 filed Mar. 27, 2024—Notice of Appeal issued Aug. 27, 2025; Machine Translation; 6 pages.

* cited by examiner

NEUROMODULATION TECHNIQUES

CROSS-REFERENCE TO RELATED APPLICATION

This application is a continuation of U.S. patent application Ser. No. 18/308,365, entitled "NEUROMODULATION TECHNIQUES", filed Apr. 27, 2023, which is a continuation of U.S. patent application Ser. No. 17/208,547, entitled "NEUROMODULATION TECHNIQUES", filed Mar. 22, 2021, which is a continuation of U.S. patent application Ser. No. 16/116,674, entitled "NEUROMODULATION TECHNIQUES", filed Aug. 29, 2018, the disclosures of which are hereby incorporated by reference in their entireties herein.

BACKGROUND

The subject matter disclosed herein relates to neuromodulation and more specifically, to neuromodulation techniques for modulating a physiological response using energy applied from an energy source.

Neuromodulation has been used to treat a variety of clinical conditions. For example, electrical stimulation at various locations along the spinal cord has been used to treat chronic back pain. An implantable device may periodically generate electrical energy that is applied to a tissue to activate certain nerve fibers, which may result in a decreased sensation of pain. With regard to spinal cord stimulation, the stimulating electrodes are generally positioned in the epidural space, although the pulse generator may be positioned somewhat remotely from the electrodes, e.g., in the abdominal or gluteal region, but connected to the electrodes via conducting wires. In other implementations, deep brain stimulation may be used to stimulate particular areas of the brain to treat movement disorders, and the stimulation locations may be guided by neuroimaging. Such central nervous system stimulation is generally targeted to the local nerve or brain cell function and is mediated by electrodes that deliver electrical pulses and that are positioned at or near the target nerves. However, positioning electrodes at or near the target nerves is challenging. For example, such techniques may involve surgical placement of the electrodes that deliver the energy. In addition, specific tissue targeting via neuromodulation is challenging. Electrodes that are positioned at or near certain target nerves mediate neuromodulation by triggering an action potential in the nerve fibers, which in turn results in neurotransmitter release at a nerve synapse and synaptic communication with the next nerve. Such propagation may result in a relatively larger or more diffuse physiological effect than desired, as current implementation of implanted electrodes stimulate many nerves or axons at once. Because the neural pathways are complex and interconnected, a more selective and targeted modulated effect may be more clinically useful.

BRIEF DESCRIPTION

Certain embodiments are summarized below. These embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, a method may include applying mechanical or ultrasound energy to a region of interest in a subject to induce modulation of one or more nerve pathways. The region of interest may include at least a portion of a nodose ganglion or a sacral ganglion.

In another embodiment, a method may include applying mechanical or ultrasound energy to a region of interest in a subject to induce modulation of two or more nerve pathways. The region of interest may include at least a portion of a nerve ganglion.

In another embodiment, a system may include an energy application device that may apply mechanical or ultrasound energy to a region of interest in a subject for modulating one or more nerve pathways, and a controller that may spatially select the region of interest, and control one or more modulation parameters of the energy application device. The region of interest may include at least a portion of a nodose or sacral nerve ganglion.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
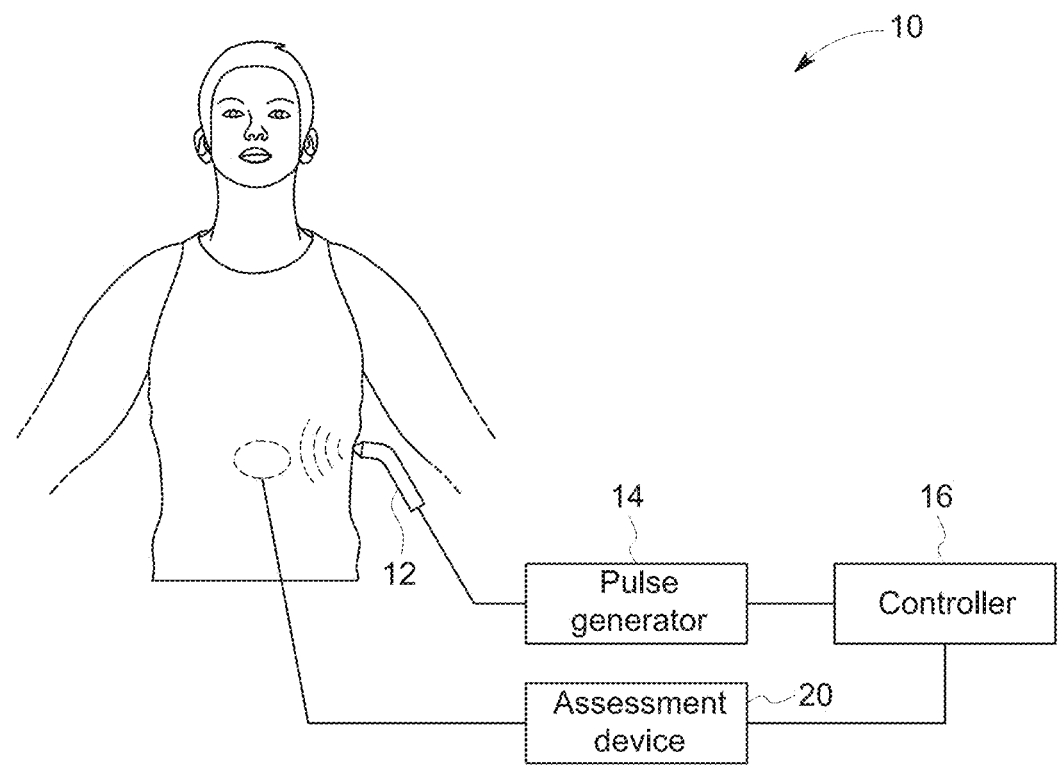
FIG. 1 is a schematic representation of a neuromodulation system according to embodiments of the disclosure.

One or more specific embodiments are described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to, "for example", "for instance", "such as", "e.g.", "including", "in certain embodiments", "in some embodiments", and "in one (an) embodiment."

When introducing elements of various embodiments of the present disclosure, the articles "a", "an", "the", and "said" are intended to mean that there are one or more of the elements. The terms "comprising", "including", and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The human nervous system is a complex network of nerve cells, or neurons, found centrally in the brain and spinal cord and peripherally in the various nerves of the body. Neurons have a cell body, dendrites, and an axon. A nerve is a group of neurons that serve a particular part of the body. Nerves may contain several hundred neurons to several hundred thousand neurons. Nerves often contain both afferent and efferent neurons. Afferent neurons carry signals to the central nervous system and efferent neurons carry signals to the periphery. The peripheral nervous system (PNS) relays signals between the central nervous system and, for example, the skin, muscles, and internal organs.

The electrical signal of a neuron is known as an action potential. Neuronal excitability is the propensity of a neuron to initiate an action potential. Action potentials are initiated when a voltage potential across the cell membrane exceeds a certain threshold activating voltage gated ion channels. This action potential is then propagated down the length of the neuron. The action potential of a nerve is complex and represents the sum of action potentials of the individual neurons in it. The junction between the axon terminals of a neuron and the receiving cell is called a synapse. Action potentials travel down the axon of the neurons to its axon terminal, which is the distal termination of the branches of an axon nerve that forms a presynaptic ending or a synaptic terminal of the nerve fiber. The electrical impulse of the action potential triggers the migration of vesicles containing neurotransmitters to a presynaptic membrane of the presynaptic axon terminal and ultimately the release of the neurotransmitters into a synaptic cleft (e.g., the space formed between the presynaptic and the postsynaptic cell) or the axoextracellular space. A synapse that converts the electrical signal of an action potential to a chemical signal by releasing neurotransmitters is a chemical synapse. In contrast to chemical synapses, electrical synapses allow ionic currents to flow into a presynaptic axon terminal and across the cell membranes into a postsynaptic cell.

The physiological effect of the action potential is mediated by ion movement across a cell membrane. Neurons actively maintain a resting membrane potential via ion pumps that facilitate movement of ions such as $Na^+$, $K^+$, and $Cl^-$ through the neuronal membrane. Different types of neurons may maintain different resting membrane potentials (e.g., −75 mV to −55 mV). An action potential is generated by an influx of ions (i.e., a movement of charge) to generate a large deviation in the membrane potential that is associated with a temporary rise in voltage across the membrane. For example, the rise in the membrane potential may be in a range of 30 mV to 60 mV. An action potential in a postsynaptic neuron may initiate in response to a release of neurotransmitters from a presynaptic (e.g., upstream) neuron. The neurotransmitters released from the presynaptic neuron bind to receptors at the postsynaptic neuron, which in turn causes an influx of ions and subsequent depolarization across the membrane. The action potential is then propagated along the nerve as this process occurs between subsequent neurons within the nerve.

Synapses may be located at a junction between two neurons, which permits an action potential to be propagated down a nerve fiber. However, axon terminals may also form synapses at the junctions between neurons and non-neuronal cells or may terminate at interstitial fluid or body fluid. Types of synapses, for example, include synapses with immune cells at a neuro-immune junction, synapses with resident sensory cells within an organ, or synapses with gland cells. The release of neurotransmitters into a synaptic cleft and the binding of the neurotransmitters to receptors in a postsynaptic membrane of a postsynaptic cell results in downstream effects that are dependent on the nature of the presynaptic neuron, the specific neurotransmitters released, and the nature of the postsynaptic cell (e.g., types of available receptors of the postsynaptic cell). Additionally, an action potential may be excitatory or inhibitory. An excitatory postsynaptic action potential increases the likelihood of the postsynaptic neuron to fire or release a subsequent action potential. In contrast, an inhibitory postsynaptic action potential decreases the likelihood of a postsynaptic neuron to fire or release a subsequent action potential. Several neurons may work together to release neurotransmitters that trigger downstream action potentials or inhibit downstream action potentials.

Neuromodulation applies energy from an external energy source to certain areas of the nervous system to activate and/or block one or more nerves or increase and/or decrease nerve function. Electrical neuromodulation applies one or more electrodes at or near target nerves, and the applied energy is carried through the nerve (e.g., as an action potential) to cause a physiological response in areas of the downstream of the energy application site. However, it is difficult to predict the scope and eventual endpoint of the physiological response for a given energy application site because of the complexity of the nervous system. While strategies for ultrasound modulation of the central nervous system (i.e. brain tissue) have demonstrated successful modulation of neural activity, attempts to modulate periph- eral nerves have lagged. For example, ultrasound modula- tion of the central nervous system (CNS) involves stimula- tion of cortical regions of the brain, which are rich in synaptic structures while attempts at ultrasound stimulation of peripheral nerves have targeted nerve trunks that are less rich in or devoid of synaptic structures. Furthermore, nerve trunks contain thousands of neuronal bundles packed tightly together, making preferential modulation of any one or set of neurons difficult. In contrast, nerve fibers in ganglion or nuclei are spaced out over millimeters to centimeters, and contains synaptic connections between incoming PNS sen- sory fiber, outgoing PNS efferent fibers, and connections to CNS neurons projecting to and from the brain. Each gan- glion serves as a communication hub for specific organ system nerve pathways, and thus provides a target for neuromodulation of one or more nerve pathways at the same time. Still further, stimulation of neurons within a nerve trunk may require activation or modulation of voltage, mechanical, or chemical gated ion channels (or other mem- brane bound proteins) within Nodes of Ranvier (i.e., the gaps within mylenated tissue in peripheral nerves). In this case, sufficient energy must be supplied to the nerve fibers to activate those channels at the Node of Ranvier to enable action potential generation and subsequent signaling to upstream or downstream fibers. However, a more varied assortment of neural structures exist within ganglion, includ- ing dendrites, axons, axonal terminal, and structures involved in both pre-synaptic and post-synaptic molecular/ neural signaling. In this case, ultrasound parameters that preferentially or more favorably stimulate or modulate spe- cific nerve structures may be found. Using these specific parameters may allow multiple outcomes, including 1) pref- erential stimulation of a large area of dendritic structure that enable cumulative ion channel activation and stimulation of action potentials, 2) preferential stimulation of cell soma, and/or 3) preferential stimulation of tissue to encourage post-synaptic versus per-synaptic activation. Spatial selec- tion of specific ganglia or nuclei or a specific location within a ganglia or nuclei may enable preferential activation or modulation of fibers associated with a specific pathway (eliminating off-target or off-pathway modulation). Addi- tionally or alternatively, stimulation of sites within specific ganglia may enable concurrent stimulation of multiple organ system pathways at one time, enabling simultaneous stimu- lation of multiple physiological systems at once, in a manner not possible with direct organ or direct CNA tissue neuro- modulation or stimulation. Finally, different position or ultrasound dependent stimulation parameters within the same ganglia (or across two or more ganglia) may allow for dynamic stimulation of multiple pathways (i.e., stimulating one more or one less than other ganglia depending on the parameter chosen).

A group or a cluster of neuronal cell bodies in one location is known as a ganglion. A ganglion of the peripheral nervous system may be located between a nerve terminus and a structure of the central nervous system (e.g., the spinal cord). Nucleic structures within the brainstem that are similar to ganglia provide connections between peripheral nerves and the brain. Pre-ganglion neurons, post-ganglionic neu- rons, inter-neurons (i.e., neurons fully contained in the ganglia), and an assortment of non-neuronal cells exist within ganglia and nuclei. Electrical signals generated in the nerves (e.g., via stimulation, which may be intrinsic or externally applied) are conducted via neurons and nerves. Neurons release neurotransmitters at synapses (connections) adjacent to a receiving cell to allow continuation and modu- lation of the electrical signals. In the peripheral nervous system, a ganglion typically serves as a relay point between the central nervous system and the rest of the body (e.g., the nerves of the limbs and the organs), and may connect to one or more anatomical systems of the body. Preganglionic fibers form synapses with postganglionic fibers in the struc- ture of the ganglion, and propagation of these nerve signals cause release of neurotransmitters as part of the ganglionic synaptic transmission. As provided herein, neuromodulation of peripheral nerve ganglia by direct energy application may result in modulation of activity in not only the ganglia to which energy has been applied, but also may cause a downstream change in one or more characteristic of organs that are innervated by the affected ganglia. This change is brought about without direct energy application to the end organ of interest. Insofar as the organs or structures of interest impact additional physiological processes (e.g., glu- cose regulation), neuromodulation of one or more peripheral nerve ganglia and, as a result, one or more downstream organs or other anatomical structures, is used to target particular targeted physiological outcomes that are local to the organ or structure of interest and/or are systemic. Fur- ther, because individual ganglia include different types of nerve fibers that innervate different locations in the body, targeting a specific ganglion of the periphery causes a specific targeted physiological outcome relative to other ganglia that, when modulated, do not cause the same effect. In this manner, targeting of a particular ganglion permits tuning of multiple targeted physiological outcomes across one or more organs or physiological systems. For instance, one might perform targeted stimulation to achieve modula- tion of inflammatory or anti-inflammatory pathways and not pathways controlled or modifying metabolism. In another example, one might perform targeted stimulation to achieve activation or modulation of one inflammatory or anti-in- flammatory pathway (i.e., controlling the output or modu- lation of a first particular cytokine or hormone) more than or less than another inflammatory or anti-inflammatory path- way (i.e., controlling the output or modulation of a second particular cytokine or hormone). One might also select and preferentially or additionally modulate secretory ganglia directly within glandular or humoral tissues. Yet another benefit is that the spatial selection of peripheral nerve ganglia for application of energy via an external device may be less complex than targeting individual nerve fibers, which are difficult to visualize.

Provided herein are techniques for neuromodulation based on direct and focused modulation of targeted region(s) of interest and to cause targeted physiological outcome(s) as a result of the neuromodulation. The targeted region(s) of interest may include at least a portion of one or more nerve ganglia. Neuromodulation of the targeted region(s) of inter- est permits a limited and non-ablative application of energy to only the targeted region(s) of interest and without apply- ing energy outside of the targeted region(s) of interest. However, energy application to the targeted region(s) of interest may trigger effects outside of the targeted region(s) of interest (e.g., in a tissue or structure containing the targeted region of interest or in an organ, tissue, or structure that does not contain the targeted region of interest). For example, energy application to synapses within peripheral nerve ganglia modulates one or more pathways based on a particular type of ganglion targeted, such as a nodose ganglion or a sacral ganglion. In some embodiments, energy application to synapses within a peripheral nerve ganglion modulates (1) a neuro-immune pathway or an anti-inflammatory pathway (e.g., the cholinergic anti-inflammatory pathway (CAP)), (2) dopamine production pathways, and/or (3) glucose regulatory or insulin production pathways. These effects outside of the targeted region(s) of interest may be achieved without direct energy application to areas outside of the targeted region(s) of interest. Accordingly, systemic effects may be realized through intermittent and non-continuous, localized energy application. Further, the effects may be realized for hours and days after the energy application. In certain embodiments, neuromodulation as provided herein may be used as a treatment for chronic disorders to alter the progression and/or to reverse the effects of chronic disorders. In one embodiment, a patient diagnosed with a disease may receive neuromodulation treatment. After the neuromodulation treatment, the patient may achieve clinical benchmarks associated with a healthy patient. For example, a patient with diabetes may exhibit abnormal blood glucose levels and/or insulin levels before neuromodulation treatment. After receiving neuromodulation treatment, the patient may have normal blood glucose levels and/or insulin levels. In another example, a patient with abnormal immune responsiveness may gain normal immune response characteristics (e.g., via altered immune cell populations, altered lymph drainage, etc.) after receiving neuromodulation treatment.

In certain embodiments, neuromodulation to targeted region(s) of interest as provided herein may exert a change in physiological processes by interrupting, decreasing, or augmenting the activation or the deactivation of one or more physiological pathways in a subject to yield a desired physiological outcome. Additionally, preferential and targeted neuromodulation may change different physiological pathways in different ways and at different locations in the body to cause an overall characteristic profile of physiological change in a subject because local energy application may result in systemic changes. Although these physiological changes may be complex, the present neuromodulation techniques provide one or more measurable physiological outcomes that are the result of targeted neuromodulation treatment and may not be achievable without the targeted neuromodulation treatment. While drug treatment and other types of intervention may yield a subset of the physiological changes caused by neuromodulation, in certain embodiments, the profile of the induced physiological changes resulting from neuromodulation treatment is unique to the neuromodulation treatment at the targeted region(s) of interest. Further, the profile of the induced physiological changes may differ between different subjects that have undergone neuromodulation treatment.

The neuromodulation techniques provided herein may also cause targeted physiological outcomes in subjects. For example, such targeted physiological outcomes may include the treatment of glucose metabolism and associated disorders, the alteration of disease progression, and the control of system inflammation. In one embodiment, neuromodulation of peripheral nerve ganglia or nuclei (such as the nucleus solitarus tractus, cervical or nodose ganglia, secretory ganglia at glandular tissue, or ganglia within humoral tissue) at region(s) of interest may be used to treat diabetes (i.e., type 1 diabetes or type 2 diabetes), hyperglycemia, sepsis, trauma, infection, diabetes-associated dementia, obesity, hyperlipidemia, metabolic dysfunction, or other eating or metabolic disorders. In another embodiment, neuromodulation may be used to promote weight loss by controlling appetite or treating cachexia, by increasing appetite. In another embodiment, neuromodulation as provided herein may alter a glucoregulatory setpoint relative to a pretreatment state to achieve treatment effects lasting for days, weeks, and/or months beyond treatment. In one example, neuromodulation at ganglia containing connections to secretory tissue (i.e. pathways leading to glands) or ganglia/nucleic containing sensory pathways in a diabetic patient may yield an initial reduction in circulating glucose relative to a baseline (before neuromodulation) during the treatment window (e.g., hours or days). This effect may be induced by preferentially and/or additionally stimulating the secretory and/or sensory pathways, and glucose reduction may be accomplished by modulating the release of hormones into circulation or by modifying glucose and/or metabolite sensing in the peripheral or central sensory cells. After treatment has concluded, while the circulating glucose may increase in the time after treatment, the increase may plateau at a new setpoint that is significantly lower than the pre-treatment setpoint.

Neuromodulation to targeted region(s) of interest may yield treatment results that persist beyond the time of treatment. Neuromodulation may alter a disease state of a patient to achieve a long-lasting result. For example, a treatment of repeated energy applications to targeted region(s) of interest over a predefined period of time may yield persistent improvement in disease symptoms. In one embodiment, the improvements are relative to untreated patients or patients treated with conventional therapies. The predefined period of time may be a time window of hours or days within which the neuromodulation treatment occurs. Additionally, the neuromodulation treatment may include one or more separate energy application events within the predefined period of time. The separate energy application events may be repeatedly administered to the same region of interest within the predefined period of time. For example, the neuromodulation treatment may occur once daily at a region of interest, whereby the once daily treatment may be according to preset modulation parameters, for two or more consecutive days.

In certain embodiments, neuromodulation may be used in conjunction with pharmaceutical therapies to alter a disease state of a patient to achieve a long-lasting result. Combinatory therapies that include neuromodulation to a targeted region(s) of interest and low-dose pharmaceuticals may achieve improved and/or more efficient physiological outcomes than pharmaceutical therapy alone. For example, neuromodulation may be used to reduce insulin resistance in patients with type-2 diabetes, thereby increasing the efficacy of initial treatment (e.g., using metformin) and reducing the need for additional pharmaceutical administration (e.g., rosiglitazone or pioglitazone).

Targeted modulation of peripheral nerve ganglia modulates one or more nerve pathways based on the particular type of ganglion or ganglia targeted, such as a nodose ganglion or a sacral ganglion. The ganglia may include synapses between preganglionic axons and postganglionic neuronal cell bodies. The disclosed synapses may be modulated to alter an activity in the synapses, e.g., a release of neurotransmitters from the preganglionic axon terminals, located in the ganglia or synapses above or below the site of stimulation. Accordingly, the altered activity may lead to local effects and/or non-local (e.g., systemic) effects. The present techniques permit energy to be focused in a targeted manner on a volume of tissue that includes one or more ganglia to achieve desired outcomes. In this manner, the targeted ganglion or ganglia within a region of interest are activated to cause downstream effects in structures innervated by the postganglionic axons. Accordingly, neuromodulation may preferentially target a specific type of ganglion, such as a nodose ganglion or a sacral ganglion, on the basis of the pathway of one or more postganglionic axons extending from the targeted ganglion.

For example, in one embodiment, the postganglionic axon may have an axon terminal forming an axoextracellular synapse with a resident (i.e., tissue-resident or non-circulating) liver, pancreatic, or gastrointestinal tissue cell. That is, the axoextracellular synapse is formed at a junction between an axon terminal and a nonneuronal cell or interstitial or body fluid. Accordingly, the application of energy leads to modulation of metabolic function outside of the region of interest but coupled to an axon extending from the region of interest. However, it should be understood that, based on the population of axon terminal types and the characteristics of the postganglionic axon and, in turn, the postsynaptic cells that form axoextracellular synapses with the postganglionic axon (e.g., immune cells, lymph cells, mucosal cells, muscle cells, etc.), different targeted physiological effects may be achieved.

In certain embodiments, the application of energy to synapses within the spleen, the liver, and the right adrenal gland may modulate a single physiological pathway, respectively. For example, ultrasound stimulation of synapses within the spleen, or a portion thereof, modulates neuro-immune pathways or anti-inflammatory pathways, such as the cholinergic anti-inflammatory pathway (CAP). In another example, ultrasound stimulation of synapses within the liver, or a portion thereof, modulates glucose regulatory and/or insulin production pathways, and ultrasound stimulation of synapses within the right adrenal gland, or a portion thereof, modulates the production of dopamine.

In certain embodiments, the application of energy to synapses within a peripheral nerve ganglion or ganglia may modulate one or more of (1) a neuro-immune pathway or an anti-inflammatory pathway, (2) dopamine production pathways, and/or (3) glucose regulatory or insulin production pathways. In other embodiments, the application of energy to synapses within a peripheral nerve ganglion or ganglia may modulate two or more physiological pathways using a single stimulation point. For example, ultrasound stimulation of a nodose ganglion, or portion thereof, modulates a neuro-immune pathway or anti-inflammatory pathway, such as the CAP and glucose regulatory and/or insulin production pathways. Additionally, ultrasound stimulation of a sacral ganglion, or portion thereof, modulates a neuro-immune or anti-inflammatory pathway, such as the CAP, and a dopamine production pathway.

Accordingly, applying energy to a region of interest in a peripheral nerve ganglion of a subject may activate axon terminals (e.g., via stimulation of axons and/or neuronal cell bodies) in the peripheral nerve ganglion and their downstream axoextracellular synapses while axon terminals (and associated synapses) that are both outside of the region of interest and that are not coupled to the ganglion in the region of interest via one or more postganglionic axons may be unaffected. However, because modulation may result in systemic effects, untargeted axon terminals outside of the region of interest may experience certain systemic changes as a result of the activation of the ganglion within the region of interest. As provided herein, preferential modulation (e.g., activation or deactivation) may refer to the inducement of the modulation of one or more targeted nerve pathways by altering the neuronal excitability within the cells or the structures of the ganglion that experiences direct application of energy within a region of interest. The region of interest may be defined as the section of tissue in which the stimulated ultrasound or other energy is focused, and all the cells both neural and non-neural within that defined anatomical region. The region of interest may be an entire ganglion (stimulated preferentially compared to other ganglion or neural tissue), a group of neurons associated with an internal ganglion with a gland or humoral tissue, a neural nuclei containing connections and synapses between the central and peripheral nervous system, or portions of any of these tissues that contain neurons associated with specific pathways (versus other pathways that pass through the same ganglia, nuclei, or tissue). That is, preganglionic axons or neuronal cell bodies of the ganglion may directly experience the applied energy as provided herein to induce downstream effects. Preferential modulation may be considered in contrast to the modulation of cells or structures in areas outside of a region of interest that do not experience direct energy application, even if such areas nonetheless undergo physiological changes as a result of the energy application.

In another example, in one embodiment, multiple postganglionic axon terminals may extend from ganglionic neuronal cell bodies. Axosynaptic synapses are formed at junctions between an axon terminal and resident cells of different anatomical systems (e.g., the digestive system, the inflammatory system, or the adrenal system) and/or different neurons. Accordingly, the application of energy may lead to modulation of one or more pathways based on the particular nerve ganglion being targeted, such as a nodose ganglion or a sacral ganglion. For example, the application of energy may lead to modulation of a neuro-immune pathway or an anti-inflammatory pathway and a dopamine production pathway, a neuro-immune pathway or an anti-inflammatory pathway and a glucose regulatory and/or insulin production pathway, a dopamine production pathway and a glucose regulatory and/or insulin production pathway, or a neuro-immune pathway or an anti-inflammatory pathway, a dopamine production pathway, and a glucose regulatory and/or insulin production pathway.

The neuromodulation techniques provided herein involve targeting one or more peripheral nerve ganglia to preferentially modulate one or more of (1) neuro-immune pathways or anti-inflammatory pathways, (2) dopamine production pathways, or (3) glucose regulatory or insulin production pathways. One or more energy pulses are applied to a subject's internal tissue containing a ganglion. The application of energy to the ganglion can cause activation of the presynaptic nerve fibers (e.g., preganglionic nerve fibers), activation of the postsynaptic nerve fibers (e.g., postganglionic nerve fibers), and/or activation or modulation of supporting cells within the tissue (i.e. resident immune or sensory cells) that modify the excitability and/or activity of the nerve fibers; any of these types of modulation can be used to cause a targeted physiological outcome. The change in activity or activation may be induction of ion channel (or other membrane protein) activity to induce action potentials in ascending or descending nerve fibers, the change in activity could be local changes in secretory functions or gene expression within the area of interest (that modifies excitability or activity of those cells), or changes in gene expression and/or secretory activity of neighboring supporting non-neuronal cells. For example, stimulation releases neurotransmitters or neuropeptides or induces an altered release of neurotransmitters and modulates nerve activity. Accordingly, modulation of other tissue structures or organs may be achieved without direct stimulation. In certain embodiments, direct energy application to a region of inter- est containing at least a portion of a peripheral nerve ganglion may result in the stimulation of action potentials in projecting neurons that project into different organs or structures (e.g., the spleen or the liver). Direct stimulation of organs or structures may result in undesired activation of other pathways that may interfere with or swamp a desired physiological outcome. Further, direct stimulation of organs or structures may involve invasive procedures. For example, the regions of the brain surrounding the hypothalamus pose an obstacle to the direct stimulation of the hypothalamus via ultrasound. Accordingly, the present techniques permit granular activation of activity within an organ or a structure in a manner that is more targeted and more specific than direct brain stimulation or electrical peripheral nerve stimu- lation. Further, the present techniques provide preferential modulation of the disclosed pathways without the use of inflammatory and/or metabolic drug therapies (e.g., anti- tumor necrosis factor (anti-TNF), insulin, or metformin).

Additionally, the ganglia modulation may involve direct activation of a relatively small region of tissue (e.g., an individual ganglion may be 5 cm or less in length) to achieve these effects. In certain embodiments, a region of interest of a subject that energy is applied to may have a surface area 1 cm$^2$ or less, 4 cm$^2$ or less, 9 cm$^2$ or less, 16 cm$^2$ or less, or 25 cm$^2$ or less. In this manner, the total applied energy is relatively small to achieve a desired physiological outcome. In certain embodiments, the applied energy may be from a non-invasive extracorporeal energy source (e.g., ultrasound energy source, mechanical vibrator). For example, a focused energy probe may apply energy through a subject's skin and is focused on a region of interest of an internal tissue. Such embodiments achieve the desired physiological outcome without invasive procedures or without side effects that may be associated with other types of procedures or therapy. Further, in certain embodiments, a peripheral nerve ganglion (e.g., a sacral ganglion or a nodose ganglion) may be closer to the skin than certain tissues or certain organs such as the liver and the spleen. The energy applied at the peripheral nerve ganglion to achieve a desired physiological outcome may be less than the energy applied to tissues or organs that are further away from the skin to achieve the same or a similar desired physiological outcome. As such, lower power systems or wearable energy application systems may be used to provide the energy applied to the peripheral nerve ganglion. To that end, the disclosed neuromodulation tech- niques may be used in conjunction with a neuromodulation system. In certain embodiments, a system may include an energy application device that may apply mechanical or ultrasound energy to a region of interest in a subject for modulating one or more nerve pathways. The system may also include a controller that may spatially select the region of interest, and control one or more modulation parameters of the energy application device to apply energy to the region of interest to induce the preferential modulation of one or more nerve pathways. Neurons within the region of interest communicate to a distal site within the subject to cause a change in concentration of one or molecules of interest at the distal site. FIG. 1 is a schematic representation of a system 10 for neuromodulation to achieve neurotrans- mitter release and/or to activate components (e.g., the post- synaptic cell) of a synapse to modulate (1) neuro-immune pathways or anti-inflammatory pathways, (2) dopamine production pathways, and/or (3) glucose regulatory or insulin production pathways in response to an application of energy. The depicted system includes a pulse generator 14 coupled to an energy application device 12 (e.g., an ultrasound transducer). The energy application device 12 is configured to receive energy pulses (e.g., via one or more leads or a wireless connection) and direct the energy pulses to a region of interest (e.g., a peripheral nerve ganglion, or a portion thereof), which in turn results in a targeted physiological outcome. In certain embodiments, the pulse generator 14 and/or the energy application device 12 may be non-invasive and extracorporeal. For example, the energy application device 12 may comprise a focused energy probe which applies energy through a subject's skin and is focused on a region of interest of an internal tissue. For example, the energy application device 12 may be a microelectrome- chanical systems (MEMS) transducer, such as a capacitive micromachined ultrasound transducer, or a dual probe.

In certain embodiments, the energy application device 12 and/or the pulse generator 14 may communicate wirelessly, for example with a controller 16 that may in turn provide instructions to the pulse generator 14. In other embodiments, the pulse generator 14 may be an extracorporeal device (e.g., may operate to apply energy transdermally or in a nonin- vasive manner from a position outside of a subject's body), and may, in certain embodiments, be integrated within the controller 16. In embodiments in which the pulse generator 14 is extracorporeal, the energy application device 12 may be operated by a caregiver and positioned at a spot on or above a subject's skin such that the energy pulses are delivered transdermally to a desired internal tissue. In cer- tain embodiments, the controller 15 may robotic or digital. Once positioned to apply energy pulses to the desired site, the system 10 may initiate neuromodulation to achieve a targeted physiological outcome or clinical effects.

In certain embodiments, the system 10 may include an assessment device 20 that is coupled to the controller 16 and is configured to assess characteristics indicative of whether the targeted physiological outcome of the modulation has been achieved. In one embodiment, the targeted physiologi- cal outcome may be local, distal, or both. For example, the modulation may result in changes to the local tissue or changes in function, such as tissue structure changes, a local change in concentration of certain molecules, tissue dis- placement, increased fluid movement, etc. In certain embodiments, the modulation may result in systemic and/or non-local (e.g., distal) changes. The targeted physiological outcome may relate to a change in concentration of circu- lating molecules or a change in a characteristic of a tissue that does not include the region of interest to which energy was directly applied. Changes may include local or distal blood flow, local or distal change in the size or position of anatomical landmarks or tissues, changes in local or circuit- ing molecular concentrations, changes in nerve activity as measured by functional imaging or electromagnetic sensors, changes in cell lipid composition and/or changes in the mechanical properties of a local or distal tissue. Accord- ingly, the assessment device 20 may be configured to assess concentration changes in some embodiments. While the depicted elements of the system 10 are shown separately, it should be understood that some or all of the elements may be combined with one another. Further, some or all of the elements may communicate in a wired or wireless manner with one another.

Based on the assessment, the modulation parameters of the controller 16 may be altered. For example, if a desired modulation is associated with a change in concentration (e.g., circulating concentration or tissue concentration of one or more molecules) within a defined time window (e.g., 5 minutes or 30 minutes after a procedure of energy application starts) or relative to a baseline at the start of a procedure, a change of the modulation parameters (e.g., pulse frequency) may be desired, which in turn may be provided to the controller 16, either by an operator or via an automatic feedback loop, for defining or adjusting the energy application parameters or modulation parameters of the pulse generator 14.

The system 10 as provided herein may provide energy pulses according to various modulation parameters. For example, the modulation parameters may include various stimulation time patterns, ranging from continuous to intermittent. With intermittent stimulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be continuous or delivered at various time periods, for example, within a day or week. The treatment duration may last over various time periods, including, but not limited to, from a few minutes to several hours. In certain embodiments, treatment duration with a specified stimulation pattern may last for one hour, repeated at, for example, 72 hour intervals. In certain embodiments, treatment may be delivered at a higher frequency, such as three hours, for shorter durations, for example, 30 minutes. Thus, the application of energy, in accordance with modulation parameters, such as the treatment duration and frequency, may be adjustably controlled to achieve a desired result.

Figure 2:
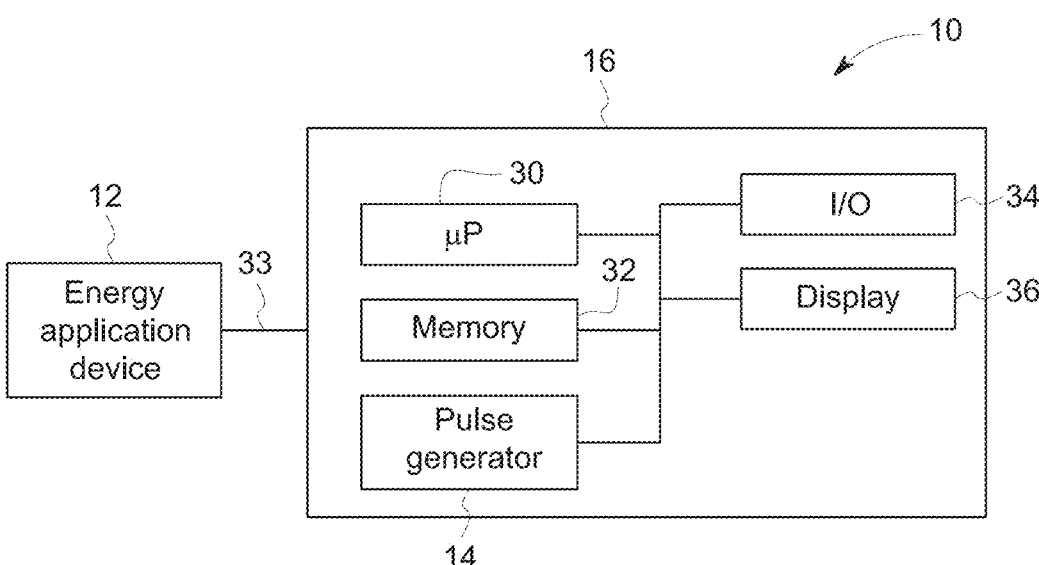
FIG. 2 is a block diagram of a neuromodulation system according to embodiments of the disclosure.

FIG. 2 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as a controller 16. The controller 16 includes a processor 30 for controlling the device. Software code or instructions are stored in memory 32 of the controller 16 for execution by the processor 30 to control the various components of the device. The controller 16 and/or the pulse generator 14 may be connected to the energy application device 12 via one or more leads 33 or wirelessly.

The controller 16 also includes a user interface with input/output circuitry 34 and a display 36 that are adapted to allow a clinician to provide selection inputs or modulation parameters to modulation programs. Each modulation program may include one or more sets of modulation parameters including pulse amplitude, pulse width, pulse frequency, etc. The pulse generator 14 modifies its internal parameters in response to control signals from the controller 16 to vary stimulation characteristics of energy pulses transmitted through lead 33 to a subject to which the energy application device 12 is applied. Any suitable type of pulse generating circuitry may be employed, including but not limited to, constant current, constant voltage, multiple-independent current or voltage sources, etc. The energy applied is a function of the current amplitude and pulse width duration. The controller 16 permits adjustably controlling the energy by changing the modulation parameters and/or initiating energy application at certain times, cancelling energy application at certain times, or suppressing energy application at certain times. In one embodiment, the adjustable control of the energy application device is based on information about a concentration of one or more molecules in the subject (e.g., a circulating molecule). If the information is from the assessment device 20, a feedback loop may drive the adjustable control. For example, if a circulating glucose concentration, as measured by the assessment device 20, is above a predetermined threshold or range, the controller 16 may initiate energy application to a region of interest (e.g., a peripheral nerve ganglion) and with modulation parameters that are associated with a reduction in circulating glucose. The initiation of energy application may be triggered by the glucose concentration drifting above a predetermined (e.g., desired) threshold or outside a predefined range. In another embodiment, the adjustable control may be in the form of altering modulation parameters when an initial application of energy does not result in an expected change in a targeted physiological outcome (e.g., concentration of a molecule of interest) within a predefined time frame (e.g., 1 hour, 2 hours, 4 hours, 1 day).

In one embodiment, the memory 32 stores different operating modes that are selectable by the operator. For example, the stored operating modes may include instructions for executing a set of modulation parameters associated with a particular treatment site (e.g., a peripheral nerve ganglion, such as a sacral ganglion or a nodose ganglion). Different sites may have different associated modulation parameters. Rather than having the operator manually input the modes, the controller 16 may be configured to execute the appropriate instruction based on the selection. In another embodiment, the memory 32 stores operating modes for different types of treatment. For example, activation may be associated with a different stimulating pressure or frequency range relative to those associated with depressing or blocking tissue function. In a specific example, when the energy application device is an ultrasound transducer, the time-averaged power (temporal average intensity) and peak positive pressure are in the range of 1 mW/cm$^2$ to 30,000 mW/cm$^2$ (temporal average intensity) and 0.1 MPa to 7 MPa (peak pressure). In one example, the temporal average intensity is less than 35 W/cm$^2$ in the region of interest to avoid levels associated with thermal damage and ablation or cavitation. In another specific example, when the energy application device is a mechanical actuator, the amplitude of vibration is in the range of 0.1 to 10 mm. The selected frequencies may depend on the mode of energy application (e.g., an ultrasound actuator or a mechanical actuator).

In another embodiment, the memory 32 stores a calibration or setting mode that permits adjustment or modification of the modulation parameters to achieve a desired result. In one example, the stimulation starts at a lower energy parameter and increases incrementally, either automatically or upon receipt of an operator input. In this manner, the operator may achieve tuning of the induced effects as the modulation parameters are being changed.

The system may also include an imaging device that facilitates focusing the energy application device 12. In certain embodiments, the imaging device may be integrated with the energy application device 12 or the imaging device may be the same device as the energy application device 12 such that different ultrasound parameters (e.g., frequency, aperture, or energy) are applied for selecting (e.g., spatially selecting) a region of interest and for focusing energy to the selected region of interest for targeting and subsequent neuromodulation. In another embodiment, the memory 32 stores one or more targeting or focusing modes that is used to spatially select the region of interest within an organ or tissue structure. Spatial selection may include selecting a region of interest that includes a peripheral nerve ganglion or a portion thereof. Based on the spatial selection, the energy application device 12 may be focused on the selected volume in a subject corresponding to the region of interest. For example, the energy application device 12 may be configured to first operate in the targeting mode to apply a targeting mode energy that is used to capture image data to be used for identifying the region of interest. The targeting mode energy is not at levels and/or applied with modulation parameters suitable for preferential activation. However, once the region of interest is identified, the controller 16 may then operate in a treatment mode according to the modulation parameters associated with preferential activation.

The controller 16 may also be configured to receive inputs related to the targeted physiological outcomes as an input to the selection of the modulation parameters. For example, when an imaging modality is used to assess a tissue characteristic that is a result of energy application to a peripheral nerve ganglion, the controller 16 may be configured to receive a calculated index or parameter of the characteristic. Based on whether the index or parameter is above or below a predefined threshold, the modulation parameters may be modified. In one embodiment, the parameter can be a measure of tissue displacement of the affected tissue or a measure of depth of the affected tissue. Other parameters may include assessing a concentration of one or more molecules of interest (e.g., assessing one or more of a change in concentration relative to a threshold or a baseline/ control, a rate of change, determining whether concentration is within a desired range). Further, the energy application device 12 (e.g., an ultrasound transducer) may operate under control of the controller 16 to (1) acquire image data of that may be used to spatially select a region of interest within the body, (2) apply the modulating energy to the region of interest, and (3) acquire image data to determine that the targeted physiological outcome has occurred. In such an embodiment, the imaging device 12, the assessment device 20 and the energy application device 12 may be the same device.

In another implementation, a desired modulation parameter set may also be stored by the controller 16. In this manner, subject-specific parameters may be determined. Further, the effectiveness of such parameters may be assessed over time. If a particular set of parameters is less effective over time, the subject may be developing insensitivity to the activated pathways. If the system 10 includes an assessment device 20, the assessment device 20 may provide feedback to the controller 16. In certain embodiments, the feedback may be received from a user or an assessment device 20 indicative of a characteristic of the target physiological outcome. The controller 16 may be configured to cause the energy application device to apply the energy according to modulation parameters and to dynamically adjust the modulation parameters based on the feedback. For example, based on the feedback, the processor 16 may automatically alter the modulation parameters (e.g., the frequency, the amplitude, or the pulse width of an ultrasound beam or a mechanical vibration) in real time and responsive to feedback from the assessment device 20.

In one example, the present techniques may be used to treat a subject with a metabolic dysfunction. The present techniques may also be used to regulate blood glucose level in subjects with glucose regulation disorders. Accordingly, the present techniques may be used to promote homeostasis of a molecule of interest or to promote a desired circulating concentration or a desired concentration range of one or more molecules of interest (e.g., glucose, insulin, glucagon, or a combination thereof). In one embodiment, the present techniques may be used to control circulating glucose levels.

In one embodiment, the following thresholds may be used to maintain blood glucose levels in a dynamic equilibrium in the normal range:

(A) Fasted:
        (1) Less than 50 mg/dL (2.8 mmol/L): Insulin Shock;
        (2) 50 mg/dL to 70 mg/dL (2.8 mmol/L to 3.9 mmol/L): low blood sugar or hypoglycemia;
        (3) 70 mg/dL to 110 mg/dL (3.9 mmol/L to 6.1 mmol/L): normal;
        (4) 110 mg/dL to 125 mg/dL (6.1 mmol/L to 6.9 mmol/L): elevated or impaired (pre-diabetic); and
        (5) 125 mg/dL (7 mmol/L): diabetic.
    (B) Non-fasted (postprandial approximately 2 hours after meal):
        (1) 70 mg/dL to 140 mg/dL (3.9 mmol/L to 7.8 mmol/L): normal;
        (2) 140 mg/dL to 199 mg/dL (8 mmol/L to 11 mmol/L): elevated or borderline (pre-diabetic); and
        (3) more than 200 mg/dL (11 mmol/L): diabetic.

For example, application of energy to a nodose ganglion (see FIG. 9) according to the disclosed techniques may be used to maintain circulating glucose concentration to be under about 200 mg/dL and/or over approximately 70 mg/dL. The techniques may be used to maintain glucose in a range between about 4 mmol/L to 8 mmol/L or about 70 to 150 mg/dL. The techniques may be used to maintain a normal blood glucose range for the subject (e.g., a patient), where the normal blood glucose range may be an individualized range based on the patient's individual factors such as weight, age, and/or clinical history. Accordingly, the application of energy to one or more regions of interest may be adjusted in real time based on the desired end concentration of the molecule of interest and may be adjusted in a feedback loop based on input from an assessment device 20. For example, if the assessment device 20 is a circulating glucose monitor or a blood glucose monitor, the real-time glucose measurements may be used as input to the controller 16.

In another embodiment, the present techniques may be used to induce a characteristic profile of physiological changes. For example, the characteristic profile may include a group of molecules of interest that increase in concentration in the tissue and/or blood as a result of the energy application and another group of molecules of interest that decrease in concentration in the tissue and/or blood as a result of the energy application. The characteristic profile may include a group of molecules that do not change as a result of the energy application. The characteristic profile may define concurrent changes that are associated with a desired physiological outcome. For example, the profile may include a decrease in circulating glucose seen together with an increase in circulating insulin.

Figure 3:
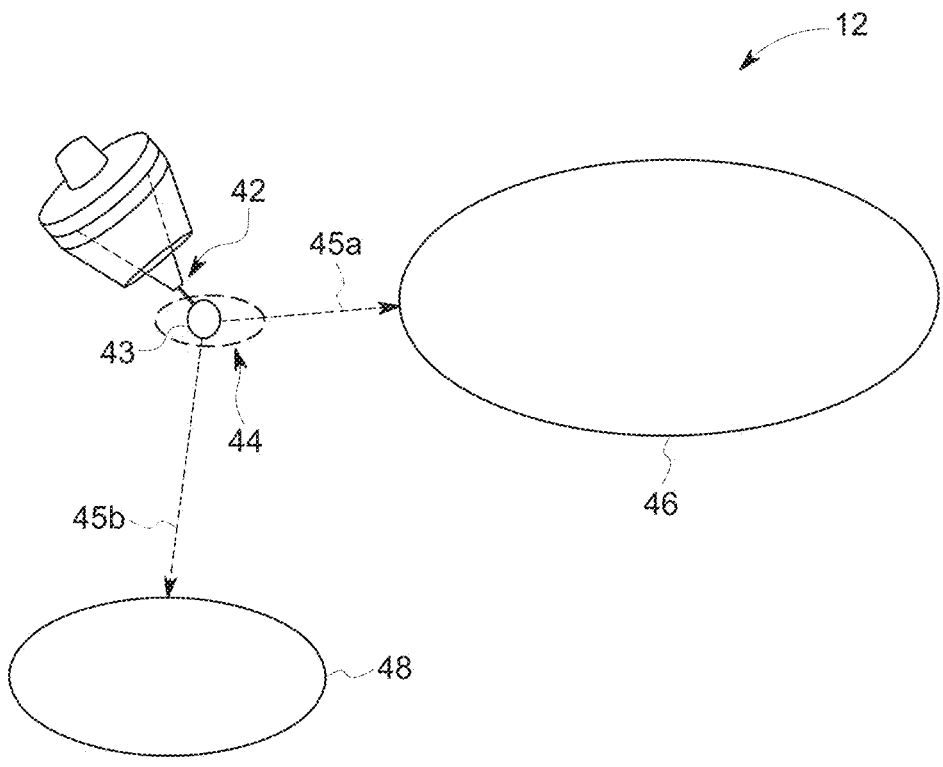
FIG. 3 is a schematic representation of an ultrasound energy application device in operation according embodiments of the disclosure.

FIG. 3 is a specific example in which the energy application device 12 includes an ultrasound transducer 42 that applies energy to a region of interest in a subject (e.g., a region of interest including a target ganglion 43 such as a peripheral nerve ganglion). The energy application device 12 may include control circuitry for controlling the ultrasound transducer 42. The control circuitry of the processor 30 may be integral to the energy application device 12 (e.g., via an integrated controller 16) or may be a separate component. The ultrasound transducer 42 may also be configured to acquire image data to assist with spatially selecting a desired or targeted region of interest and focusing the applied energy on the selected region of interest.

The desired or targeted region of interest includes a target ganglion 43, such as a peripheral nerve ganglion or a portion thereof, that includes axons that form synapses with neuronal cell bodies from which postganglionic axons 45a, 45b extend and form axoextracellular synapses within one or more downstream structures or organs (shown as organs 46, 48) or from which sensory neurons extend and form synapses with other nerves including those projecting to the central nervous system. The synapses within the target ganglion 43 may be stimulated by direct application of energy to the axon terminals within a field of focus of the ultrasound transducer 42 focused on a region of interest 44 that includes all or part of the target ganglion 43 to cause release of molecules into the synaptic space. A similar release may occur at the downstream axoextracellular synapses of the postganglionic axon, e.g., at the synapse with a liver cell, and the release of neurotransmitters and/or the change in ion channel activity may cause downstream effects such as activation of glucose metabolism. The region of interest 44 may be selected to include a certain type of ganglion 43, such as one that includes a neuronal cell body that includes a postganglionic axon of a particular neuron type and/or that forms a synapse with a certain type of non-neuronal cell. Accordingly, the region of interest 44 may be selected to correspond to the target ganglion 43 with desired postganglionic axon terminals (and associated non-neuronal cells). In certain embodiments, the energy application may be selected to preferentially trigger a release of one or more molecules (e.g., neurotransmitters) from the nerve within the synapse. In certain embodiments, the energy application may be selected to preferentially trigger a release of one or more molecules (e.g., neurotransmitters) by directly activating a neuronal cell in the region of interest 44 through direct energy transduction (i.e. mechanotransduction or voltage-activated proteins within the non-neuronal cells). In certain embodiments, the energy application may be selected to preferentially trigger a release of one or more molecules (e.g., neurotransmitters) by causing an activation within neuronal cells within the region of interest 44 that elicits a desired physiological effect.

The energy may be focused or substantially concentrated on a region of interest 44 and to all or only part of the target ganglion 43 (e.g., less than about 75%, 50%, 25%, 10%, or 5% of the total volume of the ganglion 43). In one embodiment, energy may be applied to a region of interest 44 that is larger than the target ganglion 43, e.g., about 105% to about 200% of the volume of the ganglion 43, to include an entirety of the target ganglion 43. In one embodiment, energy may be applied to two or more regions target ganglia 43. In one embodiment, the energy is applied to only about 1% to 50% of the total volume of the ganglion 43 or to about 25% to 100% of the total volume of the ganglion 43. In certain embodiments, the energy may be focused or concentrated within a volume of less than about 25 mm$^3$. In certain embodiments, the energy may be focused or concentrated within a volume of about 0.5 mm$^3$ to 50 mm$^3$. A focal volume and a focal depth for focusing or concentrating the energy within the region of interest 44 may be influenced by the size or the configuration of the energy application device 12. The focal volume of the energy application may be defined by the field of focus of the energy application device 12. For example, for an ultrasound transducer, the field of focus may be defined by an ultrasound lens attached to the surface of the ultrasound transducer or the arrangement of the transducer elements of the ultrasound transducer. The field of focus defines the size and/or shape of the energy from the energy application device 12 into the subject and to the region of interest 44. As provided herein, the energy may be substantially applied only to the region or the region(s) of interest 44 to preferentially activate the ganglion 43. Accordingly, only a subset of a plurality of different types of ganglia in the body are exposed to the direct energy application.

Figure 4:
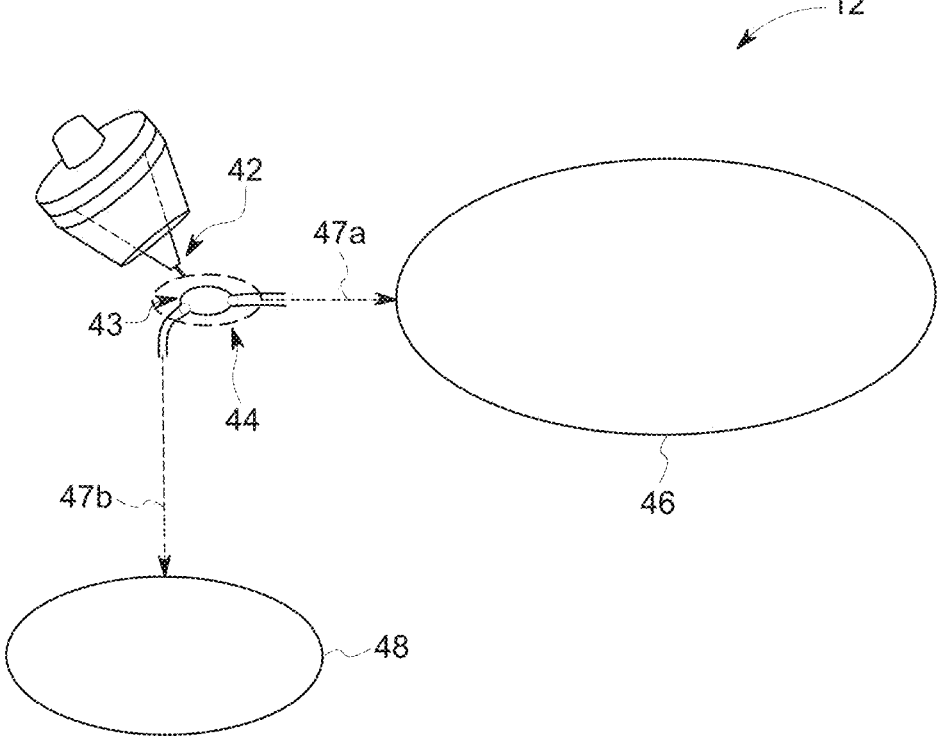
FIG. 4 is a schematic representation of an ultrasound energy application device applying energy to a sacral ganglion according embodiments of the disclosure.

The region(s) of interest 44 containing the ganglia 43 may be identified by imaging, reference to anatomical landmarks (e.g., the carotid arch), etc., to perform the spatial selection. FIG. 4 is an example in which the energy application device 12 includes an ultrasound transducer 42 that applies energy to a region of interest 44 containing a sacral ganglion 43. The region of interest 44 may be chosen based on the point of entry 47a of the sacral ganglion 43 into an organ 46 or point of entry 47b of the sacral ganglion into a bone structure 48. Referring back to FIG. 3, an individual ganglion 43 included in the region of interest may be selected based on factors including, but not limited to, historical or experimental data (e.g., data showing an association of a particular location with a desired or targeted physiological outcome). Alternatively or additionally, the system 10 may apply energy to a region of interest containing individual ganglia 43, or portions thereof, until the desired targeted physiological effect is achieved. The disclosed selection of ganglia 43 for preferential activation via a direct energy application to a region of interest using spatial information of visualized nerves may be used in conjunction with other organs or structures (e.g., liver, pancreas, or gastrointestinal tissue).

In other embodiments, the region(s) of interest may be identified by the presence or the absence of one or more biological markers. Such markers may be assessed by staining tissue and obtaining images indicative of the stain to identify regions of the tissue that include the biological marker(s). In some embodiments, the biological marker information may be obtained by in vivo staining technologies to obtain location data of the biological marker(s) within the subject in real time. In other embodiments, the biological marker information may be obtained by in vitro staining technologies to obtain location data from one or more representative images that is used to predict the locations of the biological marker(s) within the subject. In some embodiments, the region of interest is selected to correspond with tissue that is rich in a particular biological marker or that lack a particular biological marker. For example, the one or more biological markers may include markers for neuronal structures (e.g., myelin sheath markers).

The region of interest in the organ or tissue may be spatially selected based on operator input. For example, an operator may designate the region of interest on an acquired image by directly manipulating the image (e.g., drawing or writing the region of interest on the image) or by providing image coordinate information that corresponds to the region of interest. In another embodiment, the region of interest may be automatically selected based on the image data to achieve spatial selection. In some embodiments, the spatial selection includes storing data related to the region of interest in a memory and accessing the data.

The disclosed techniques may be used in the assessment of neuromodulation effects, which in turn may be used as an input or a feedback for selecting or modifying neuromodulation parameters. The disclosed techniques may use direct assessments of tissue condition or function as the targeted physiological outcomes. The assessment may occur before (i.e., baseline assessment), during, and/or after the neuromodulation.

The assessment techniques may include at least one of: functional magnetic resonance imaging, diffusion tensor magnetic resonance imaging, positive emission tomography, diagnostic imaging ultrasound, or acoustic monitoring, thermal monitoring. The assessment techniques may also include protein and/or marker concentration assessment. The images from the assessment techniques may be received by the system for automatic or manual assessment. Based on the image data from the assessment techniques, the modulation parameters may be modified. For example, a change in tissue size or displacement may be utilized as a marker of local neurotransmitter concentration, and used as a surrogate marker for exposure of local cells to phenotype modulating neurotransmitters, and effectively as a marker of a predicted effect on glucose metabolic pathways or systemic inflammation pathways (e.g., neuro-immune or anti-inflammatory pathways or dopamine production pathways). The local concentration may refer to a concentration within a field of focus of the energy application.

Additionally or alternatively, the system may assess the presence or concentration of one or more molecules in a tissue region or in the blood. The concentration in the tissue may be referred to as a local concentration or resident concentration. Tissue may be acquired by a fine needle aspirate, and the assessment of the presence or levels of molecules of interest (e.g., metabolic molecules, markers of metabolic pathways, peptide transmitters, catecholamines) may be performed by any suitable technique known to one of ordinary skilled in the art.

Figure 5:
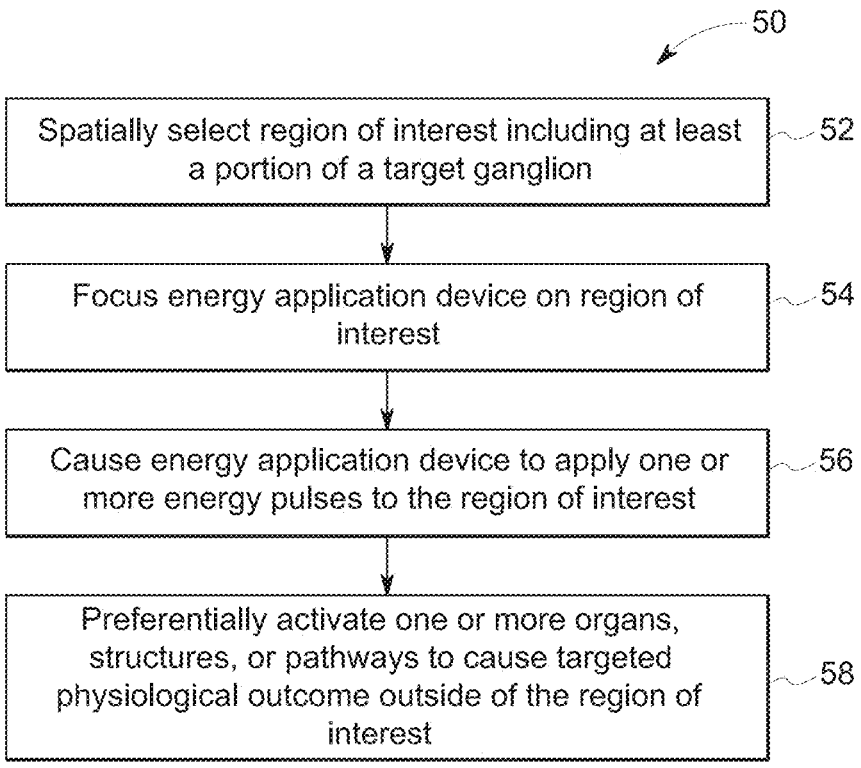
FIG. 5 is a flow diagram of a neuromodulation technique according to embodiments of the disclosure.

FIG. 5 is a flow diagram of a method 50 for stimulating a peripheral nerve ganglion. In the method 50, the region of interest is spatially selected 52. The energy application device is positioned such that the energy pulses are focused at the desired region of interest at step 54, and the pulse generator applies a plurality of energy pulses to the region of interest of the target tissue at step 56 to activate synapses in the target ganglion, for example, to stimulate the axon terminal to release neurotransmitters and/or induce altered neurotransmitter release and/or induce altered activity neuronal cell body (within the synapse) to cause a targeted physiological outcome, e.g., by preferentially activating one or more organs, structure or pathways, at step 58 as provided herein. In certain embodiments, the method may include a step of assessing the effect of the stimulation. For example, one or more direct or indirect assessments of a state of ganglion function or condition may be used. Based on the function as assessed, the modulation parameters of the one or more energy pulses may be modified (e.g., dynamically or adjustably controlled) to achieve the targeted physiological outcome.

In one embodiment, assessments may be performed before and after applying energy pulses to assess a change in concentration of one or more molecules of interest (e.g., glucose, TNF, acetylcholine (ACh), norepinephrine (NE), or dopamine (DA)) as a result of the modulation. If the concentration of the molecule(s) of interest are above or below a threshold, appropriate modification in the modulation parameters may be made. For example, if the glucose concentration is not congruent with the desired physiological outcome, the energy applied during neuromodulation may be stepped back to a minimum level that supports the desired outcome. If the change in the molecule(s) of interest relative to the threshold is associated with an insufficient change in the molecule(s) of interest, certain modulation parameters, including, but not limited to, the modulation amplitude or frequency, the pulse shape, the stimulation pattern, and/or the stimulation location, may be changed.

Further, the assessed characteristic or condition may be a value or an index, for example, a flow rate, a concentration, a cell population, or any combination thereof, which in turn may be analyzed by a suitable technique. For example, a relative change exceeding a threshold may be used to determine if the modulation parameters are modified. The desired modulation may be assessed via a measured clinical outcome, such as a presence or absence of an increase in tissue structure size (e.g., lymph node size) or a change in concentration of one or more released molecules (e.g., relative to the baseline concentration before the neuromodulation). In one embodiment, a desired modulation may involve an increase in concentration above a threshold (e.g., above about a 50%, 100%, 200%, 400%, 1000% increase in concentration relative to a baseline). For blocking treatments, the assessment may involve tracking a decrease in concentration of a molecule over time (e.g., at least a 10%, 20%, 30%, 50%, or 75% decrease in concentration of the molecule of interest). Further, for certain subjects, the desired blocking treatment may involve keeping a relatively steady concentration of a particular molecule in the context of other clinical events that may tend to increase the concentration of the molecule. That is, desired blocking may block a potential increase. The increase or decrease or other induced and measurable effect may be measured within a certain time window from the start of a treatment (e.g., within about 5 minutes or within about 30 minutes).

In certain embodiments, if the physiological outcome of the neuromodulation is determined to be desired, a change in the neuromodulation may act as an instruction to stop applying energy pulses. In another embodiment, one or more parameters of the neuromodulation may be changed if the physiological outcome of the neuromodulation is not desired. For example, the change in modulation parameters may be an increase in pulse repetition frequency, such as a stepwise increase in frequency of 10 Hz to 100 Hz, and assessment of the desired characteristic continues until a desired physiological outcome of the neuromodulation is achieved. In another implementation, a pulse width may be changed. In other embodiments, two or more of the parameters may be changed together (e.g., in parallel or in series). If the physiological outcome of the neuromodulation is not desired after multiple parameter changes, the focus (i.e., the site) of energy application may be changed.

The energy application device 12 may be configured as an extracorporeal, non-invasive device or an internal device (e.g., a minimally invasive device). As described herein, the energy application device 12 may be an extracorporeal, non-invasive ultrasound transducer or mechanical actuator. For example, the energy application device 12 may be configured as a handheld ultrasound probe including an ultrasound transducer. However, it should be understood that other noninvasive implementations are also contemplated, including other methods to configure, adhere, or place ultrasound transducer probes over an anatomical target. Further, in addition to handheld configurations, the energy application device 12 may include steering mechanisms responsive to instructions from the controller 16. The steering mechanisms may orient or direct the energy application device 12 towards a target ganglion 43 (or structure), and the controller 16 may then focus the energy application onto the region of interest 44.

Figure 6:
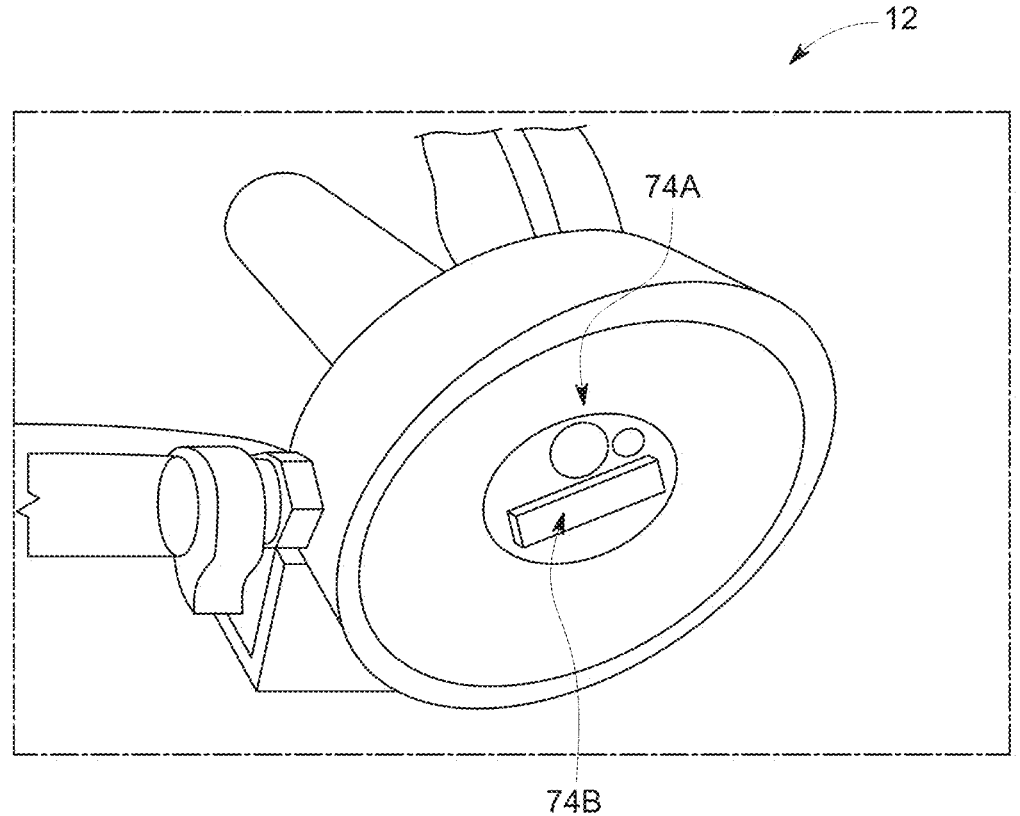
FIG. 6 is a schematic representation of an energy application device that may be employed within the neuromodulation system of FIG. 1 according to embodiments of the disclosure.

FIG. 6 is an example of an energy application device 12 that may be used in conjunction with the system 10 of FIG. 1 including a high intensity focused ultrasound (HIFU) transducer 74A and an imaging ultrasound transducer 74B arranged in a single energy application device 12 that may be controlled (e.g., by the controller 16) to apply energy and to image the target tissue as provided herein.

Examples

Ultrasound Targeting for Specific Peripheral Nerve Ganglion Neuromodulation

A GE Vivid E9 ultrasound system and an 11 L probe were used for the ultrasound scan before neuromodulation started. A focal area corresponding to an interior region of interest was labeled on animal skin. The HIFU transducer was positioned on the labeled area. Another ultrasound scan was also performed using a smaller imaging probe (3S), which was placed in the opening of the HIFU transducer. The imaging beam of the 3S probe was aligned with the HIFU beam. Therefore, one could confirm that the HIFU beam was targeted at the region of interest using an image of the targeted organ (visualized on the ultrasound scanner).

Animal Subjects, Ultrasound Stimulation Protocol, and Tissue Analysis

Adult male Sprague-Dawley rats, 8 to 12 weeks old (250-300 g; Charles River Laboratories), were housed at 25° C. on a 12-hour light/dark cycle and acclimatized for 1 week before experiments were conducted. Water and regular rodent chow were available ad libitum.

LPS-Induced Inflammation and Hyperglycemia

Endotoxin (LPS from *Escherichia coli,* 0111: B4; Sigma-Aldrich) was used to produce a significant state of inflammation and metabolic dysfunction (e.g. hyperglycemia and hyperinsulemia) in naïve adult-Sprague Dawley rats. LPS was administered to animals (10 mg/kg; Rosa-Ballinas PNAS, 2008) via intraperitoneal (IP) injection causing significant elevation in TNF and circulating glucose concentration which peaks at 4 hours post injection, but remains elevated as compared to control for up to 8 hours post injection. Neuromodulation using applied ultrasound energy was performed on the spleen, the right adrenal gland, a sacral ganglion, a nodose ganglion, and/or nucleus tractus solitaries. The ultrasound application was performed for 1 minute before and after LPS injection. Blood samples were collected 15 minutes after the last ultrasound treatment to analyze changes in circulating catecholamine concentration (e.g., norepinephrine and dopamine). Terminal blood samples were collected 60 minutes after the last ultrasound treatment to analyze changes in circulating TNF concentration. Blood samples were stored with the anti-coagulant (disodium) EDTA to prevent coagulation of samples. Samples were analyzed by ELISA assay for changes in TNF (Lifespan) and acetylcholine (Lifespan) concentration. Catecholamine (e.g., norepinephrine and dopamine) concentrations were assessed using HPLC detection or ELISA (Rocky Mountain Diagnostic) analysis.

Ultrasound Stimulation Protocols:

(A) Animals were anesthetized with 2-4% isoflurane.

(B) The animals were laid prone on a water circulating warming pad to prevent hyperthermia during the procedure.

(C) The region above the targeted region of interest for ultrasound stimulus (e.g., nerve of interest) were shaved with a disposable razor and animal clippers prior to stimulation.

(D) Diagnostic imaging ultrasound was used to spatially select the region of interest.

(E) The area was marked with a permanent marker for later identification.

(F) Either an FUS ultrasound probe or a LogiQ E9 probe was placed at the designated region of interest previously identified by the diagnostic imaging ultrasound.

(G) An ultrasound pulse was then performed with a total duration of a single stimulus not surpassing a single 1-minute pulse. Energies of the ultrasound pulses would not reach levels associated with thermal damage and ablation or cavitation (e.g., 35 W/cm$^2$).

(H) LPS (10 mg/kg may then be injected intraperitoneal (for acute or kinetic studies). Alternatively, for duration of effect, LPS may instead be injected at a later designated time point.

(I) A second 1-minute ultrasound pulse may be applied.

(J) The animal may then be allowed to incubate under anesthesia for acute study (e.g., 1 hour) and kinetic study (e.g., varying up to a maximum of 3 hours post LPS). After which the animal is sacked and tissue and blood samples are collected.

Tissue Harvesting and Sample Preparation

An incision was made starting at the base of the peritoneal cavity extending up and through to the pleural cavity. Organs were rapidly removed and homogenized in a solution of PBS, containing phosphatase (0.2 mM phenylmethylsulfonyl fluoride, 5 μg/mL of aprotinin, 1 mM benzamidine, 1 mM sodium orthovandate and 2 μM cantharidin) and protease (1 μL to 20 mg of tissue as per Roche Diagnostics) inhibitors. A targeted final concentration of 0.2 g tissue per mL PBS solution was applied in all samples. Blood samples were stored with the anti-coagulant (disodium) EDTA to prevent coagulation of samples. Samples were then stored at −80° C. until analysis. Samples were analyzed by ELISA assay for changes in TNF (Lifespan/Abcam/ThermoFisher) concentration and acetylcholine (Lifespan) concentration. Catecholamine concentrations were assessed using high performance liquid chromatography (HPLC) detection or enzyme-linked immunosorbent assay (ELISA) (Rocky Mountain Diagnostic) analysis.

HPLC Analyses

Serum samples were injected directly into HPLC with no pre-treatment. Tissue homogenates were initially homogenized with 0.1 M perchloric acid and centrifuged for 15 minutes. The supernatant was then separated and the sample was injected into the HPLC.

Catecholamines (e.g., norepinephrine and dopamine) were analyzed by HPLC with an inline ultraviolet detector. The test column used in this analysis was a Supelco Discovery C18 (15 cm×4.6 mm I.D., 5 μm particle size). A biphasic mobile phase comprised of [A] acetonitrile: [B] 50 mM KH$_2$PO$_4$, set to pH 3 (with phosphoric acid). The solution was then buffered with 100 mg/L EDTA and 200 mg/L 1-octane-sulfonic acid. Final concentration of the mobile phase mixture was set at 5:95 (A:B). A flow rate of 1 mL/min was used to improve overall peak resolution while the column was held to a consistent 20° C. to minimize pressure compaction of the column resulting from the viscosity of the utilized mobile phase. The UV detector was maintained at 254 nm, which is a wavelength known to capture the absorption for catecholamines (e.g., norepinephrine and dopamine).

Figure 7:
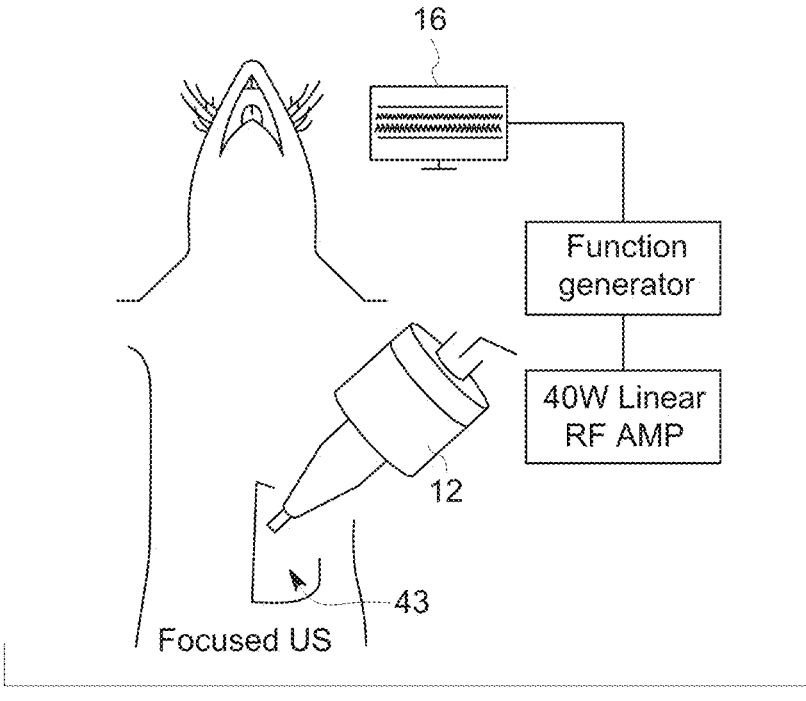
FIG. 7 is a schematic illustration of an experimental setup for ultrasound energy application to achieve target physiological outcomes according to embodiments of the disclosure.

FIG. 7 shows an experimental setup used to perform certain neuromodulation experiments focused on a target ganglion 43 (e.g., containing a peripheral nerve ganglion, or portion thereof) as provided herein. The energy application device 12 may operate according to parameters set by the controller 16 to apply energy to a region of interest in the target ganglion 43. As discussed herein, the target tissue may include a peripheral nerve ganglion, or portion thereof, such as a sacral ganglion or a nodose ganglion. While the depicted experimental setup is shown with a 40 W RF amplifier, this is by way of example only, and other amplifiers (e.g., linear amplifiers) may be used. In certain setups, the rat heads are inserted in a birdcage coil.

An experimental timeline for ultrasound energy application used to perform certain modulation experiments is provided herein. Ultrasound application was performed for one minute before and after lipopolysaccharide injection. Lipopolysaccharides (LPS) are bacterial membrane molecules that elicit a strong immune or inflammatory response. LPS from *Escherichia coli* 0111: B4 (Sigma-Aldrich) was used to produce a significant state of inflammation and metabolic dysfunction (e.g. hyperglycemia and insulin resistance) in naïve adult-Sprague Dawley (SD) rats. LPS was administered to animals (10 mg/kg) via intraperitoneal (IP) injection causing significant elevation in concentrations of TNF, glucose, and insulin. These concentrations peaked at one hour and typically persisted for up to four hours but remained elevated as compared to the control for up to eight hours post injection. The control included LPS-sham rats (e.g., rats injected with LPS and ultrasound transducers were placed on the rats without application of the ultrasound stimulus). The animals were sacrificed at a time period (e.g., one hour) after the ultrasound treatment of ganglia or nuclei for organ harvesting and processing.

The present examples demonstrate a noninvasive method to stimulate specific axonal projections of neurons in a particular peripheral nerve ganglion that lead to non-neuronal cells and/or other neurons using ultrasound energy application to achieve stimulation and an associated physiological outcome. For example, application of energy to synapses within a particular peripheral nerve ganglion may modulate (1) neuro-immune or anti-inflammatory pathways, (2) dopamine production pathways, (3) glucose regulatory or insulin production pathways, and/or (4) cognitive processing and plasticity.

CAP response to local ultrasound stimulation was monitored by measuring blood concentrations of CAP-related neurotransmitters and cytokines including norepinephrine (NE), acetylcholine (ACh), and tumor necrosis factor (TNF). Ultrasound stimulation of a sacral ganglion and a nodose ganglion were found to achieve modulation of the concentration of NE and TNF in the blood. This result is similar to or correlates with ultrasound stimulation of the spleen and the axons associated with the CAP pathway to modulate the concentration of NE and TNF. Additionally, ultrasound stimulation of a sacral ganglion and a nodose ganglion were found to achieve modulation of the concentration of dopamine in the blood. This result is similar to or correlates with ultrasound stimulation of the right adrenal gland and the axons associated with the production of dopamine. Further, ultrasound stimulation of a nodose ganglion was shown to modulate sensory pathways that regulate blood glucose circulation. Collectively, this data demonstrates that ultrasound neuromodulation within peripheral nerve ganglia could offer methods for precision neuromodulation that facilitates stimulating subsets of neurons within a peripheral nerve ganglion to affect specific physiological pathways (e.g., modulation of neuro-immune pathways, anti-inflammatory pathways, dopamine production pathways, and/or glucose regulatory or insulin production pathways). Specifically, ultrasound stimulation focused on subsets of axons and synapses within a sacral ganglion may affect systemic inflammation (e.g., decrease systemic inflammation) through neuro-immune pathways or anti-inflammatory pathways and/or may affect systemic inflammation (e.g., decrease systemic inflammation) through the production of dopamine in the right adrenal gland. Additionally, ultrasound stimulation focused on subsets of axons and synapses within a nodose ganglion may affect systemic inflammation (e.g. decrease systemic inflammation) through neuro-immune or anti-inflammatory pathways, may affect systemic inflammation (e.g., decrease systemic inflammation) through the production of dopamine in the right adrenal gland, and/or may maintain glucose homeostasis.

Figure 8A:
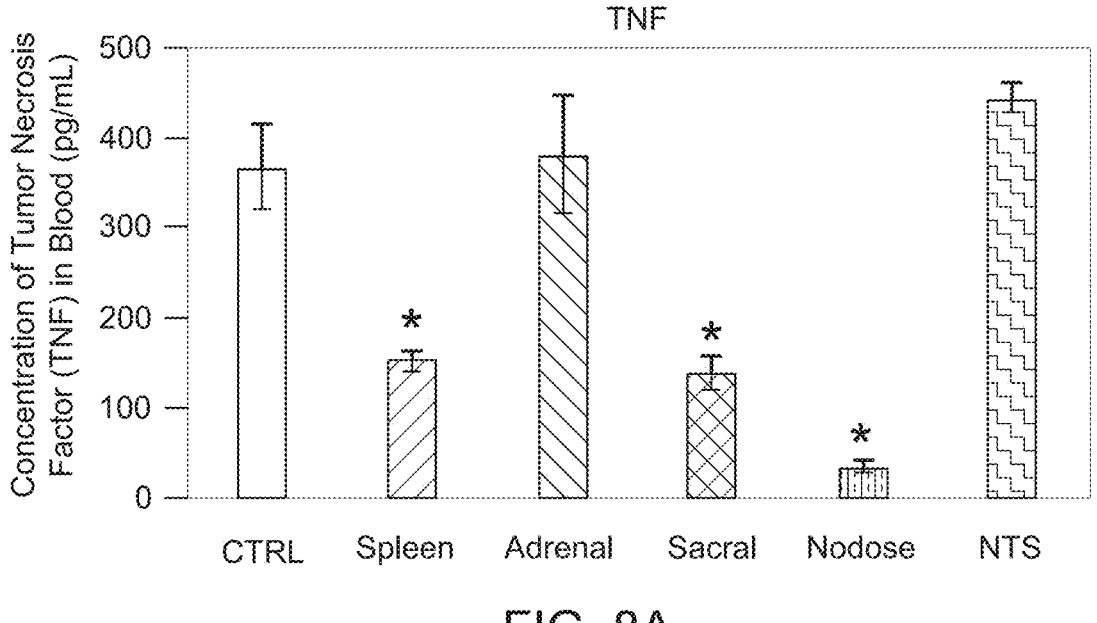
FIG. 8A shows the concentration of tumor necrosis factor (TNF) in blood after ultrasound energy application to spleen, right adrenal gland, a sacral ganglion, a nodose ganglion, and nucleus tractus solitarii (NTS) of Lipopolysaccharides (LPS)-induced hyperglycemia animal models according to embodiments of the disclosure.
Figure 8B:
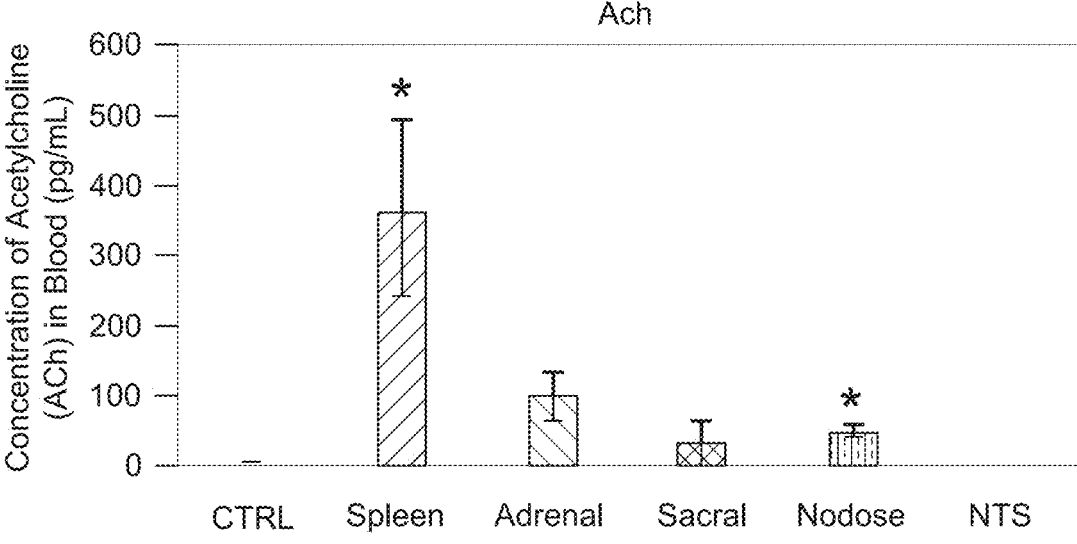
FIG. 8B shows the concentration of acetylcholine (ACh) in blood after ultrasound energy application to spleen, right adrenal glands, sacral ganglia, nodose ganglia, and NTS of LPS-induced hyperglycemia animal models according to embodiments of the disclosure.
Figure 8C:
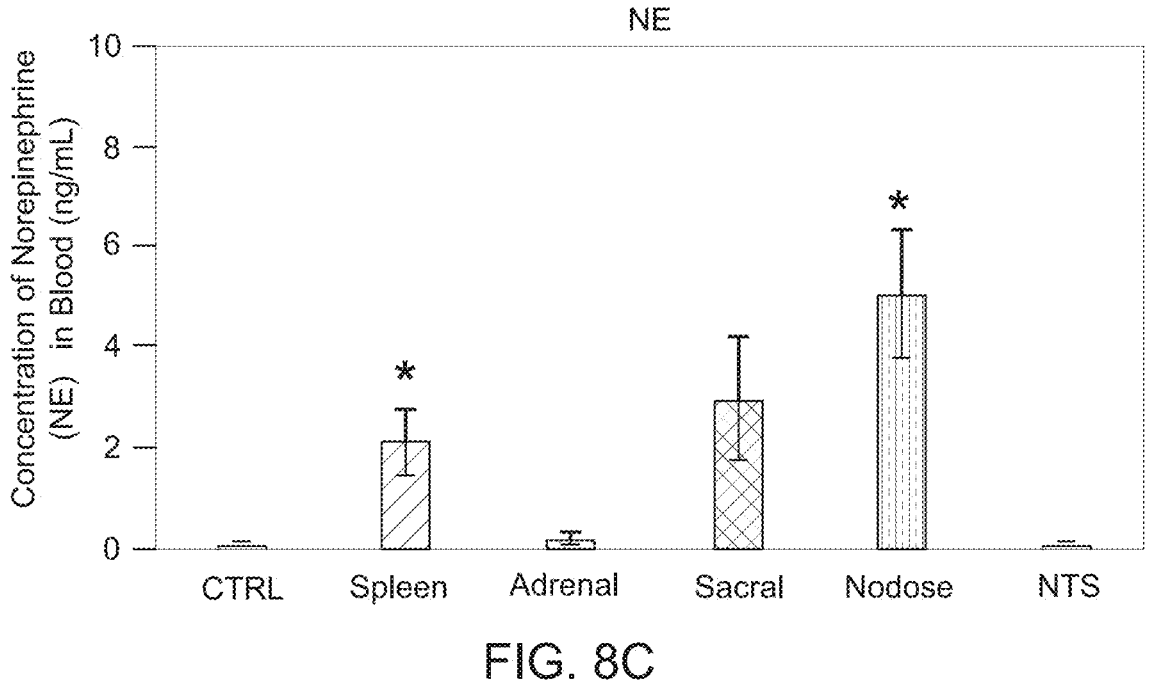
FIG. 8C shows the concentration of norepinephrine (NE) in blood after ultrasound energy application to spleen, right adrenal gland, a sacral ganglion, a nodose ganglion, and NTS of LPS-induced hyperglycemia animal models according to embodiments of the disclosure.
Figure 8D:
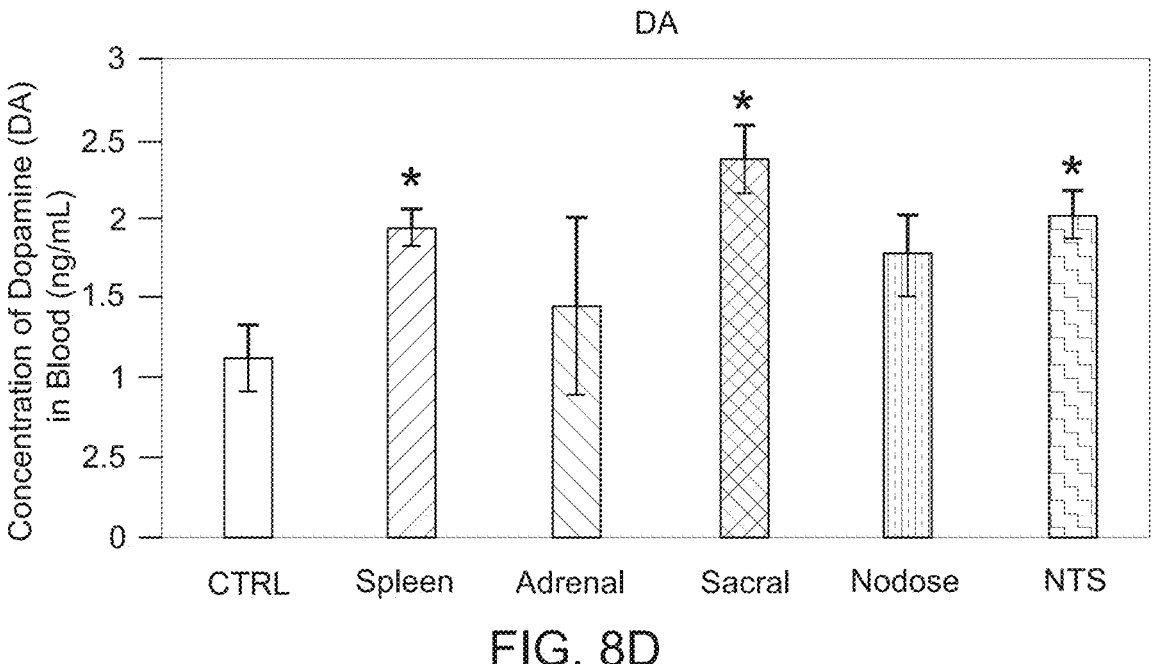
FIG. 8D shows the concentration of dopamine (DA) in blood after ultrasound energy application to spleen, right adrenal gland, a sacral ganglion, a nodose ganglion, and NTS of LPS-induced hyperglycemia animal models according to embodiments of the disclosure.

FIGS. 8A to 8D show the average concentrations of various neurotransmitters and cytokines relative to a control after ultrasound stimulation of the spleen, a right adrenal gland, a sacral ganglion, a nodose ganglion, or the nucleus tractus solitarii. FIG. 8A shows the average TNF concentration (and the standard deviation) in the blood after ultrasound treatment of the disclosed targeted regions of interest. FIG. 8B shows the average acetylcholine concentration (and the standard deviation) in the blood after ultrasound treatment of the disclosed targeted regions of interest. FIG. 8C shows the average NE concentration (and the standard deviation) in the blood after ultrasound treatment of the disclosed targeted regions of interest. FIG. 8D shows the average DA concentration (and the standard deviation) in the blood after ultrasound treatment of the disclosed targeted regions of interest. As shown in FIG. 8A, ultrasound stimulation of a sacral ganglion and a nodose ganglion produced results that were similar to ultrasound stimulation of the spleen and the axons associated with the CAP pathway to decrease the concentration of TNF relative to the control. As shown in FIGS. 8B and 8C, the increase in the concentration of NE in the blood as a result of ultrasound stimulation of the spleen, the sacral ganglion, and the nodose ganglion produced an increase in the concentration of acetylcholine in the blood. As shown in FIG. 8D, ultrasound stimulation of a sacral ganglion, produced results that were similar to ultrasound stimulation of the right adrenal gland and the axons associated with the production of dopamine. As such, ultrasound modulation within a peripheral nerve ganglia (e.g., a sacral ganglion or a nodose ganglion) affects one or more specific physiological pathways (e.g., modulation of neuro-immune pathways, anti-inflammatory pathways, dopamine production pathways, glucose regulatory pathways, and/or insulin production pathways) based on the particular peripheral nerve ganglion being stimulated. Specifically, ultrasound modulation within nodose ganglia modulates a neuro-immune pathway or anti-inflammatory pathway, such as the CAP, and glucose regulatory and/or insulin production pathways. Additionally, ultrasound modulation within sacral ganglia modulates a neuro-immune pathway or an anti-inflammatory pathway, such as the CAP, and a dopamine production pathway.

Figure 9:
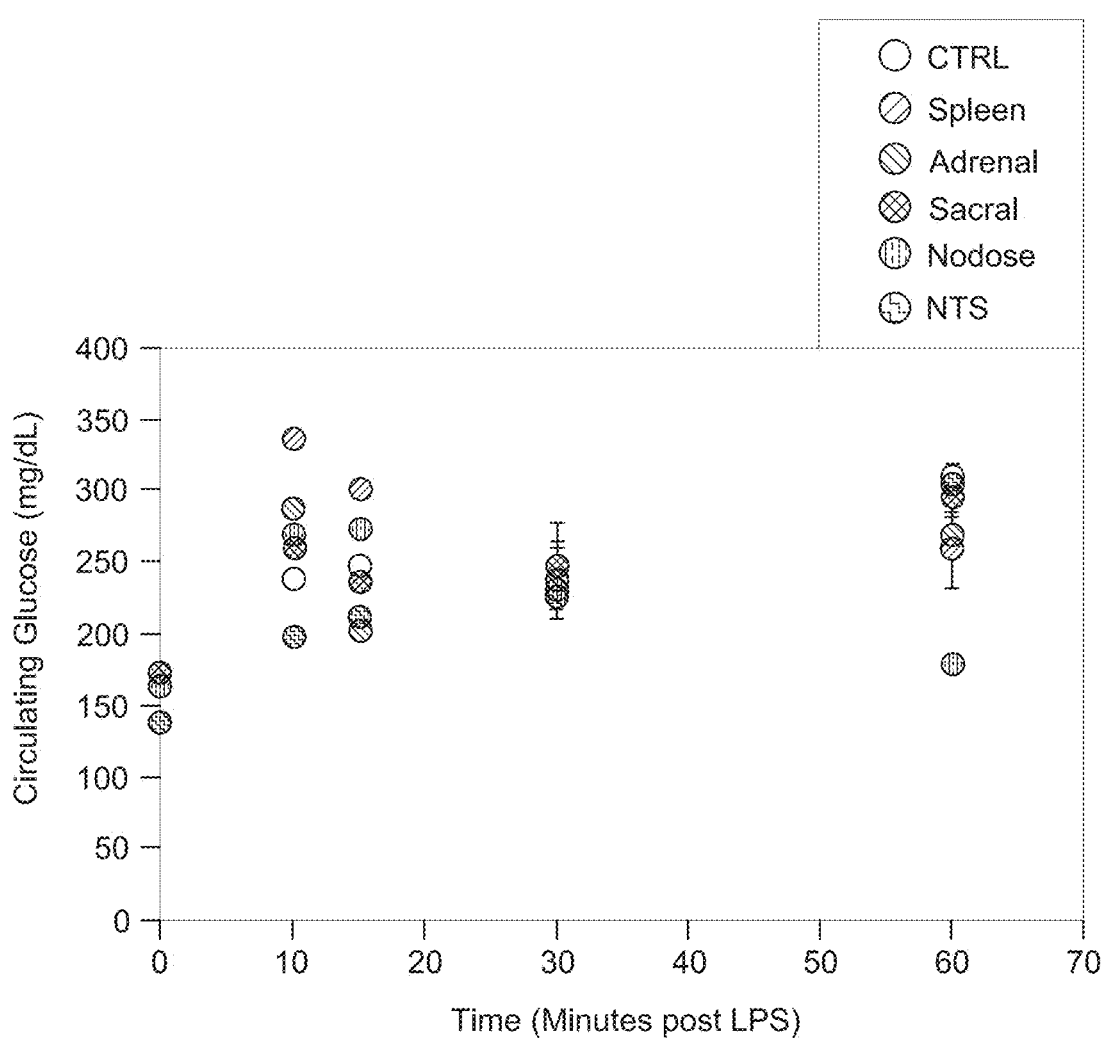
FIG. 9 shows the effect of ultrasound energy application to spleen, right adrenal gland, a sacral ganglion, a nodose ganglion, and NTS of LPS-induced hyperglycemia animal models according to embodiments of the disclosure.

FIG. 9 provides a non-limiting example of preferentially applying ultrasound stimulation to various regions of LPS-induced hyperglycemia animal model to achieve targeted modulation of blood glucose concentration. The plot of FIG. 9 shows relative blood glucose concentrations at time points of 10, 15, 30, and 60 minutes after LPS injection compared to pre-LPS injection blood glucose concentrations at the time point of 0 minutes. In a group that receives only LPS injection without ultrasound stimulation, LPS-induced hyperglycemia is observed. Although no significant difference in circulating glucose concentration followed ultrasound stimulation to the right adrenal gland, the sacral ganglia (e.g., sacral dorsal root ganglia, and spatially selected by targeting of the sacral plexus), and NTS relative to the control, a significant decrease in circulating glucose concentration relative to the control followed ultrasound stimulation to the nodose ganglia. As such, preferentially applying ultrasound stimulation to the nodose ganglia is used to reverse LPS-induced hyperglycemia and modulate blood glucose concentration.

Accordingly, ultrasound neuromodulation within a nodose ganglion affects glucose regulatory and/or insulin production pathways. As shown in the embodiment of FIG. 9, applying ultrasound stimulation to a nodose ganglion provides protection against LPS-induced hyperglycemia of the model and limits and/or controls the increase of blood glucose concentration. Thus, ultrasound energy application to a nodose ganglion may be used as a protective treatment or as a treatment applied in advance of an anticipated systemic challenge or disruption.

Figure 10:
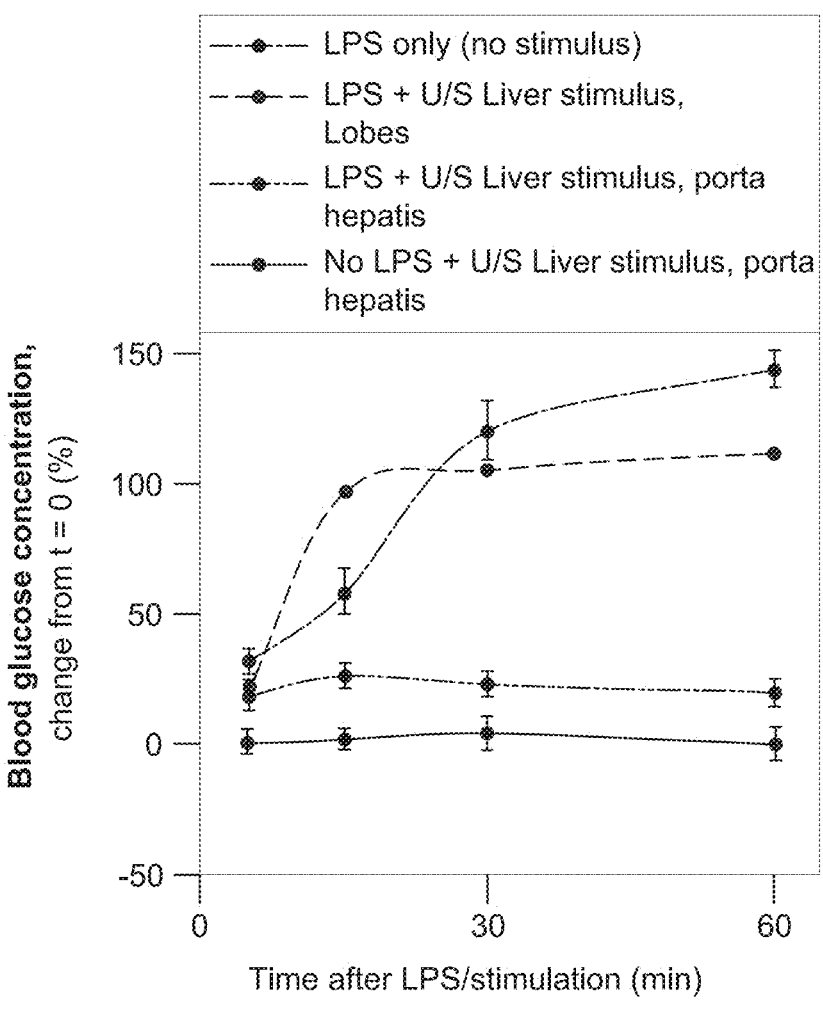
FIG. 10 shows the effect of ultrasound energy application to liver of LPS-induced hyperglycemia animal models according to embodiments of the disclosure.

FIG. 10 provides a non-limiting example of preferentially applying ultrasound stimulation to the liver of LPS-induced hyperglycemia animal models to achieve targeted modulation of blood glucose concentration. The plot of FIG. 12 shows relative blood glucose concentrations at time points of 5, 15, 30, and 60 minutes after LPS injection. In a group that receives only LPS injection without ultrasound stimulus, LPS-induced hyperglycemia is observed. The data further shows that ultrasound stimulation of the distal lobes of the liver does not significantly affect the blood glucose concentration. In contrast, preferentially applying ultrasound stimulation on the porta hepatis may be used to reverse LPS-induced hyperglycemia and modulate blood glucose concentration.

The disclosed techniques as provided herein employ the natural hierarchical structure and organization of the nervous system, permitting precision neuromodulation with a simple, noninvasive technology. For example, application of energy to a peripheral nerve ganglion may modulate one or more of (1) neuro-immune pathways or anti-inflammatory pathways, (2) dopamine production pathways, and/or (3) glucose regulatory or insulin production pathways using a single stimulation point. As such, stimulation of a peripheral nerve ganglion, or a portion thereof, may enable modulation of one of the disclosed pathways, two of the disclosed pathways, or three of the disclosed pathways based on the particular peripheral nerve ganglion being stimulated. While demonstrated for the disclosed nerve pathways, the techniques may be applied to modulate other peripheral nerve circuits. Additionally, overall less energy may be applied to a peripheral nerve ganglion to achieve a desired physiological outcome relative to deeper positioned organs and tissues beneath the skin. As such, lower power systems or wearable energy application systems may be used to provide the energy applied to a peripheral nerve ganglion.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system, comprising:
an energy application device configured to apply non-invasive and non-ablative ultrasound energy to at least a portion of a nerve plexus or at least a portion of a ganglion in a subject to modulate one or both of a neuro-immune pathway or an anti-inflammatory pathway, wherein at least the portion of the nerve plexus or at least the portion of the ganglion innervate a spleen of the subject, and wherein modulation of one or both of the neuro-immune pathway or the anti-inflammatory pathway treats one or more of sepsis, cell or tissue trauma, or infection; and
a controller configured to control the energy application device to apply the non-invasive and non-ablative ultrasound energy to at least the portion of the nerve plexus or at least the portion of the ganglion.

2. The system of claim 1, wherein the ganglion comprises a peripheral nerve ganglion.

3. The system of claim 1, wherein the anti-inflammatory pathway comprises a cholinergic anti-inflammatory pathway (CAP).

4. The system of claim 1, wherein one or more physiological effects associated with the modulation of the neuro-immune pathway or the anti-inflammatory pathway persist for hours or days after the application of the non-invasive and non-ablative ultrasound energy.

5. The system of claim 1, wherein modulation of one or both of the neuro-immune pathway or the anti-inflammatory pathway causes the subject to exhibit normal immune response characteristics after application of the non-invasive and non-ablative ultrasound energy, wherein prior to application of the non-invasive and non-ablative ultrasound energy the subject exhibits abnormal immune responsiveness.

6. The system of claim 1, wherein modulation of one or both of the neuro-immune pathway or the anti-inflammatory pathway causes one or both of an alteration in progression of a disease or control of inflammation in the subject.

7. The system of claim 1, wherein the energy application device is configured to acquire ultrasound image data of the nerve plexus or the ganglion prior to applying the non-invasive and non-ablative ultrasound energy and wherein the non-invasive and non-ablative ultrasound energy is applied based on the ultrasound image data.

8. The system of claim 1, wherein the controller is configured to receive as feedback a concentration or change in concentration of a molecule of interest corresponding to an immune response or to systemic or tissue inflammation.

9. The system of claim 8, wherein the controller is configured to receive as feedback a concentration or change in concentration of tumor necrosis factor (TNF).

10. A method, comprising:
acquiring ultrasound image data of a subject;
identifying a nerve plexus or a ganglion of the subject within the ultrasound image data; and
modulating one or both of a neuro-immune pathway or an anti-inflammatory pathway in a subject by applying, via an energy application device, non-invasive and non-ablative ultrasound energy to at least a portion of the nerve plexus or at least a portion of the ganglion, wherein at least the portion of the nerve plexus or at least the portion of the ganglion innervate a spleen of the subject, and wherein modulation of one or both of the neuro-immune pathway or the anti-inflammatory pathway treats one or more of sepsis, cell or tissue trauma, or infection.

11. The method of claim 10, wherein the ganglion comprises a peripheral nerve ganglion.

12. The method of claim 10, wherein modulating one or both of the neuro-immune pathway or the anti-inflammatory pathway causes the subject to exhibit normal immune response characteristics after application of the non-invasive and non-ablative ultrasound energy, wherein prior to application of the non-invasive and non-ablative ultrasound energy the subject exhibits abnormal immune responsiveness.

13. The method of claim 10, further comprising:

receiving as feedback a concentration or change in concentration of a molecule of interest corresponding to an immune response or to systemic or tissue inflammation.

14. One or more computer-readable media storing processor-executable code on a tangible medium, the one or more computer-readable media comprising:

code for acquiring ultrasound image data of a subject;

code for identifying a nerve plexus or a ganglion of the subject within the ultrasound image data; and code for modulating one or both of a neuro-immune pathway or an anti-inflammatory pathway in a subject by applying, via an energy application device, non-invasive and non-ablative ultrasound energy to at least a portion of the nerve plexus or at least a portion of the ganglion, wherein at least the portion of the nerve plexus or at least the portion of the ganglion innervate a spleen of the subject, and wherein modulation of one or both of the neuro-immune pathway or the anti-inflammatory pathway treats one or more of sepsis, cell or tissue trauma, or infection.

15. The one or more computer-readable media of claim 14, wherein modulating one or both of the neuro-immune pathway or the anti-inflammatory pathway causes the subject to exhibit normal immune response characteristics after application of the non-invasive and non-ablative ultrasound energy, wherein prior to application of the non-invasive and non-ablative ultrasound energy the subject exhibits abnormal immune responsiveness.

16. The one or more computer-readable media of claim 14, further comprising:

code for receiving as feedback a concentration or change in concentration of a molecule of interest corresponding to an immune response or to systemic or tissue inflammation.

\* \* \* \* \*